(12) United States Patent
Finn et al.

(10) Patent No.: US 8,563,738 B2
(45) Date of Patent: Oct. 22, 2013

(54) LIGANDS FOR COPPER-CATALYZED AZIDE-ALKYNE CYCLOADDITION REACTIONS

(75) Inventors: M. G. Finn, San Diego, CA (US); Valentin O. Rodionov, Rockville, MD (US)

(73) Assignee: The Scripps Research Institute, La Jolla, CA (US)

( * ) Notice: Subject to any disclaimer, the term of this patent is extended or adjusted under 35 U.S.C. 154(b) by 345 days.

(21) Appl. No.: 12/733,730

(22) PCT Filed: Sep. 15, 2008

(86) PCT No.: PCT/US2008/010739
§ 371 (c)(1),
(2), (4) Date: Mar. 17, 2010

(87) PCT Pub. No.: WO2009/038685
PCT Pub. Date: Mar. 26, 2009

(65) Prior Publication Data
US 2010/0197871 A1    Aug. 5, 2010

Related U.S. Application Data

(60) Provisional application No. 60/994,487, filed on Sep. 18, 2007.

(51) Int. Cl.
*C07F 1/08* (2006.01)
*C07D 403/14* (2006.01)

(52) U.S. Cl.
USPC ........................ 548/108; 548/305.4

(58) Field of Classification Search
USPC .............................. 548/108, 305.4
See application file for complete search history.

(56) References Cited

U.S. PATENT DOCUMENTS

2007/0020620 A1 * 1/2007 Finn et al. .................. 435/5

OTHER PUBLICATIONS

Thompson et al. "Complexes of substituted benzothiazoles. 2. Copper(II) complexes of the 'tripod' ligand tris(2-benzothiazolylmethyl)amine" Canadian Journal of Chemistry, 1980, vol. 58, pp. 1566-1576.*
Hendriks et al "Dimeric copper(II) compounds with a tripodal imidazole-containing ligand and bridged by imidazolate, benzimidazolate, and benzotriazolate ions. Crystal and molecular structure of μ-(benzotriazolato-N1,N3)bis{[tris(N1-methylbenzimidazol-2-ylmethyl)amine-N,N3,N3',N"]copper(II)} trinitrate" J. Chem. Soc. Dalton Trans. 1982 p. 621-631.*
Müller-Hartmann et al. "Diphosphate-Zinc Complexes with Encapsulating Tripodal Coligands" Eur. J. Inorg. Chem., 2000, vol. 2000, pp. 2371-2377.*
Su et al. "Chemistry of tripodal ligands. Part III.: Copper complexes of tris(benzimidazol-2-ylmethyl)amine and of its N-n-propyl derivative" Tetrahedron, 1999, vol. 18, pp. 1577-1585.*

* cited by examiner

*Primary Examiner* — Joseph Kosack
(74) *Attorney, Agent, or Firm* — Olson & Cepuritis, Ltd.

(57) ABSTRACT

Ligands useful for promoting copper-catalyzed azide-alkyne cycloaddition reactions comprise a compound represented by structural Formula (I) as described in the specification, wherein in Formula (I) $Z^1$ is a nitrogen-containing heterocyclic group or a group represented by the formula: $Y^1$—$(CH_2)_c$—$Y^2$—$(CH_2)_d$—$Y^3$—$CH_2$—$N(CH_2Z^4)(CH_2Z^5)$, where $Y^1$ is -$E^1$-C(O)O—, -$E^1$-C(O)NH—, -$E^1$-, or a covalent bond; $Y^2$ is a covalent bond, —CH=CH—, or a 1,4-(1,2,3-triazolyl) group; $Y^3$ is —OC(O)-$E^2$-, —NHC(O)-$E^2$-, -$E^2$-, or a covalent bond; each of $E^1$ and $E^2$ is a benzimidazolyl group attached at the 1 and 2 positions; each of c and d is independently 1, 2, 3, 4, or 5; each of $Z^2$, $Z^3$, $Z^4$ and $Z^5$ is a nitrogen-containing heterocyclic group including a substituent $X^1$ and optionally including a substituent $(CH_2)_n$—$R^1$, and $Y^1$, $Y^2$, $Y^3$, $X^1$, $R^1$, c, d and n are each as defined in the specification.

2 Claims, 14 Drawing Sheets

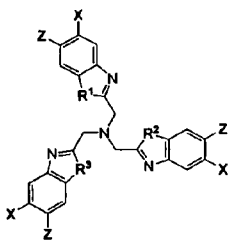

| | R¹ | R² | R³ | X | Z |
|---|---|---|---|---|---|
| (BimH)₃ | N-H | N-H | N-H | H | H |
| (Bth)(BimH)₂ | S | N-H | N-H | H | H |
| (Bth)₂(BimH) | S | S | N-H | H | H |
| (BimH/S)₃ | N-H | N-H | N-H | SO₃H | H |
| (BimH/Me₂)₃ | N-H | N-H | N-H | Me | Me |
| (BimC₁H)₃ | N-CH₃ | N-CH₃ | N-CH₃ | H | H |
| (BimC₃H)₃ | N⌒Me | N⌒Me | N⌒Me | H | H |
| (BimC₁E)₃ | N⌒CO₂Et | N⌒CO₂Et | N⌒CO₂Et | H | H |
| (BimC₁E')₃ | N⌒CO₂tBu | N⌒CO₂tBu | N⌒CO₂tBu | H | H |
| (BimC₁A)₃ | N⌒CO₂K | N⌒CO₂K | N⌒CO₂K | H | H |
| (BimC₃A)₃ | N⌒⌒CO₂K | N⌒⌒CO₂K | N⌒⌒CO₂K | H | H |
| (BimH)₂(BimC₄A) | N-H | N-H | N⌒⌒⌒CO₂K | H | H |
| (Bth)(BimC₄A)₂ | S | N⌒⌒⌒CO₂K | N⌒⌒⌒CO₂K | H | H |
| (BimC₄E)₃ | N⌒⌒⌒CO₂Et | N⌒⌒⌒CO₂Et | N⌒⌒⌒CO₂Et | H | H |
| (BimC₄A)₃ | N⌒⌒⌒CO₂K | N⌒⌒⌒CO₂K | N⌒⌒⌒CO₂K | H | H |
| (BimC₄A/Me₂)₃ | N⌒⌒⌒CO₂K | N⌒⌒⌒CO₂K | N⌒⌒⌒CO₂K | Me | Me |
| (BimH)(BimC₅A)₂ | N-H | N⌒⌒⌒⌒CO₂K | N⌒⌒⌒⌒CO₂K | H | H |
| (BimC₅A)₃ | N⌒⌒⌒⌒CO₂K | N⌒⌒⌒⌒CO₂K | N⌒⌒⌒⌒CO₂K | H | H |

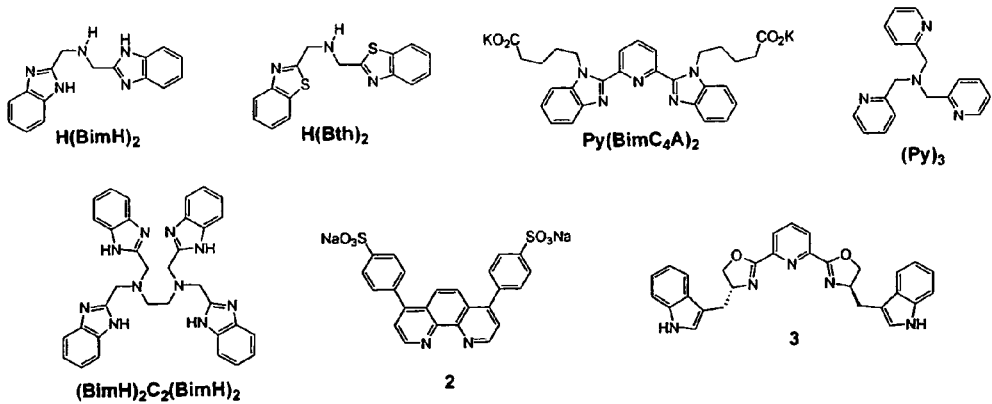

Figure 1C

| Entry | Ligand | Cu(I) source | mol % Cu | mol % ligand | Time, h | Yield (%)[a] |
|---|---|---|---|---|---|---|
| 1 | 1 | CuSO4-ascorbate | 0.1 | 0.2 | 24 | 27 |
| 2 | 1 | CuSO4-ascorbate | 0.5 | 0.5 | 4.5 | 47 |
| 3 | (BimH)3 | CuSO4-ascorbate | 1 | 1 | 5 | 94 |
| 4 | (BimH)3 | CuSO4-ascorbate | 0.5 | 0.5 | 5 | 92 |
| 5 | (BimH)3 | [Cu(MeCN)4]OTf | 1 | 1 | 24 | 93 |
| 6 | (BimH)3 | CuI | 1 | 1 | 24 | 6 |
| 7 | (BimH)3 | CuSO4-ascorbate | 0.1 | 0.1 | 24 | 73 |
| 8 | (BimC4A)3 | CuSO4-ascorbate | 0.5 | 0.5 | 0.2 | 100 |
| 9 | (BimC4A)3 | CuSO4-ascorbate | 0.05 | 0.05 | 5 | 98 |
| 10 | (BimC4A)3 | CuSO4-ascorbate | 0.01 | 0.01 | 24 | 95 |
| 11 | (BimC4A)3 | CuSO4-ascorbate | 0.005 | 0.005 | 72 | 35 |
| 12 | iPr2EtN | CuI[b] | 0.5 | 5 | 72 | 29 |

LIGANDS FOR COPPER-CATALYZED AZIDE-ALKYNE CYCLOADDITION REACTIONS

CROSS-REFERENCE TO RELATED APPLICATIONS

This application claims the benefit of U.S. Provisional Application Ser. No. 60/994,487, filed Sep. 18, 2007, which is incorporated herein by reference.

FIELD OF INVENTION

The invention relates to ligands for metal ions. More particularly, the invention relates to ligands for copper that are useful for promoting copper-catalyzed azide-alkyne cycloaddition reactions and methods of use thereof.

BACKGROUND

Unlike the well established thermal Huisgen cycloaddition reaction (Huisgen, R. In 1,3-*Dipolar Cycloaddition Chemistry*; Padwa, A., Ed.; Wiley: New York, 1984; Vol. 1, p 1-176), the Cu-catalyzed version thereof disclosed in U.S. Pat. No. 7,375,234 to Sharpless et al., offers consistent 1,4-stereoselectivity, is not limited to highly activated alkynes, and proceeds efficiently even at micromolar concentrations of reactants in aqueous media. Many investigators have reported the use of amines as copper-binding ligands and/or protic bases to aid azide-alkyne cycloaddition reactions, including 2,6-lutidine, triethylamine, N,N,N'-trimethylethylenediamine, diisopropylethylamine, proline, AMBERLYST® A21 amine resin, and other aliphatic amines. The most commonly used ligand for copper-catalyzed azide-alkyne cycloadditions has been tris((1-benzyl-1H-1,2,3-triazol-4-yl)methyl)amine (TBTA, 1) discovered by the Sharpless laboratory (Chan, T. R.; et al. *Org. Lett.* 2004, 6, 2853-2855).

There is an ongoing need for copper ligands to further enhance the rate, efficiency and/or efficacy of the copper-catalyzed azide-alkyne cycloaddition reactions. The present invention fulfills this need.

SUMMARY OF THE INVENTION

Described herein are the preparation, comparative kinetic evaluation, and practical use of several improved families of multidentate copper ligands comprising a plurality of heterocyclic groups capable of coordinating with copper, for promoting copper-catalyzed azide-alkyne cycloaddition ("CuAAC") reactions. The ligands of the invention comprise a one or more tertiary amines bearing nitrogen heterocycle substituents.

A ligand of the present invention comprises a compound represented by structural Formula (I):

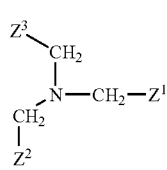

Formula (I)

wherein $Z^1$ is a nitrogen-containing heterocyclic group or $-Y^1-(CH_2)_c-Y^2-(CH_2)_d-Y^3-CH_2-N(CH_2Z^4)(CH_2Z^5)$. In Formula (I), $Y^1$ is $-E^1-C(O)O-$, $-E^1-C(O)NH-$, $-E^1-$, or a covalent bond; $Y^2$ is a covalent bond, $-CH=CH-$, or a 1,4-(1,2,3-triazolyl) group; $Y^3$ is $-OC(O)-E^2-$, $-NHC(O)-E^2-$, $-E^2-$, or a covalent bond; each of c and d is independently 1, 2, 3, 4, or 5; and each of $Z^2$, $Z^3$, $Z^4$ and $Z^5$ is a nitrogen-containing heterocyclic group. Each of $E^1$ and $E^2$ is a benzimidazolyl group attached at the 1 and 2 positions. Each of the nitrogen-containing heterocyclic groups in Formula (I) bears at least one substituent, $X^1$, and optionally bears a substituent, $-(CH_2)_n-R^1$. Each nitrogen-containing heterocyclic group in the compound is independently selected from the group consisting of a 2-benzimidazolyl group, a 2-benzothiazolyl group, a 2-pyridyl group, a 2-oxazolinyl group, a 2-oxazolyl group, a 1-(1,2,3-triazolyl) group, a 4-(1,2,3-triazolyl) group, a 5-(1,2,3-triazolyl) group, and optionally an azoferrocenyl group. Each $X^1$ is independently selected from the group consisting of H, phenyl, benzyl, a halogen, $-SO_3M$, $-SO_3H$, $C_1$-$C_6$-alkyl, and $C_1$-$C_6$-alkoxy. Each $R^1$ is independently selected from the group consisting of $-C(O)OH$, $-C(O)OM$, $-C(O)OR^2$, $-C(O)NHR^3$, and $-C(O)R^4$; wherein each M is an alkali metal ion or ammonium ion; each $R^2$ and $R^3$ is independently a $C_1$-$C_6$-alkyl group; each $R^4$ is independently H or a $C_1$-$C_6$-alkyl group; and each n is independently 1, 2, 3, 4, 5, 6, 7, 8, 9, or 10.

When $Z^1$ is a nitrogen-containing heterocyclic group, and each heterocyclic group in the compound is a 2-benzimidazolyl group, and none of the 2-benzimidazolyl groups includes a $-(CH_2)_n-R^1$ substituent, then at least one of the 2-benzimidazolyl groups of the ligand also includes an $X^1$ substituent that is not H, $-SO_3M$, or $-SO_3H$; however, when at least one of the 2-benzimidazolyl groups includes a $-(CH_2)_n-R^1$ substituent, then at least one of the 2-benzimidazolyl groups also includes an $X^1$ substituent that is not H, or at least one other 2-benzimidazolyl group includes a $-(CH_2)_n-R^1$ substituent.

When $Z^1$ is a nitrogen-containing heterocyclic group, and each heterocyclic group in the compound is a 2-pyridyl group, then at least one of the 2-pyridyl groups includes an $X^1$ substituent that is not H.

When $Z^1$ is a nitrogen-containing heterocyclic group, and at least one of the heterocyclic groups is a 4-(1,2,3-triazolyl) group, then at least one other of the heterocyclic groups of the compound is not a 4-(1,2,3-triazolyl) group.

In certain preferred embodiments, the ligand of Formula (I) includes at least one 2-benzimidazolyl group, at least one 2-benzothiazolyl group, at least one a 2-pyridyl group, at least one 2-oxazolinyl group, or any combination thereof.

In other preferred embodiments, the ligand of Formula (I) includes at least one 2-benzimidazolyl group and at least one ligand selected from a 2-pyridyl group, a 2-benzothiazolyl group, and a 4-(1,2,3-triazolyl) group.

In certain preferred embodiments, the heterocyclic groups in the ligand of Formula (I) are all 2-benzimidazolyl groups, all 2-benzothiazolyl groups, all 2-pyridyl groups, or all 2-oxazolidinyl groups.

The present invention also provides substrate-bound ligands. The substrate-bound ligands comprise a ligand of Formula (I) bound to a solid support such as polymeric beads (e.g., polystyrene beads) or a glass substrate. The ligand of Formula (I) preferably is bound to the substrate via an $X^1$ substituent, e.g., by chemically reacting a functional group of the substituent with a reactive group on the substrate or vice versa (e.g., by formation of an ester or amide bond between the substituent and the substrate, alkylation of an amino group, and the like). Methods for binding organic ligands to substrates are well known in the organic chemical arts.

In another aspect, the present invention provides a copper complex comprising a ligand of Formula (I) complexed with a copper ion, such as a Cu(I) ion, a Cu(II) ion, or any combination thereof.

The present invention also provides a method of promoting a copper-catalyzed azide-alkyne cycloaddition reaction. The method comprises contacting an azide (e.g., an organic azide) and an alkyne (preferably a terminal alkyne) with a source of Cu(I) ion in the presence of a ligand of Formula (I). The ligands of the invention promote the cycloaddition reaction by coordinating with a copper (I) ion to form a complex. The complexed Cu(I) then is believed to coordinate with an azide and an alkyne, bringing the azide and alkyne into proper orientation for the cycloaddition reaction to occur, thereby forming a 1,2,3-triazole compound. If desired, the copper (I) ion can be formed in situ by reaction of Cu(II) or ligand-complexed Cu(II) with a reducing agent such as ascorbic acid, which is capable of reducing Cu(II) to Cu(I), as is known I the art.

The ligands of the present invention enhance the rate and/or efficiency of CuAAC reactions relative to the rate and/or efficiency of a CuAAC reaction performed with the same combination of azide and alkyne under the same reaction conditions (e.g., concentration, temperature, solvent, etc.) in the absence of the ligand. In addition, the ligands of the present invention are useful as chelating or complexing agents for a variety of metal ions, including but not limited to copper, regardless of their efficacy for enhancing the rate or efficiency of CuAAC reactions.

BRIEF DESCRIPTION OF DRAWINGS

FIG. 1C illustrates the basic structure of various ligands along with the names or abbreviations used herein to refer to the ligands. The changes in the substitution pattern made in each succeeding ligand are given in bold.

DETAILED DESCRIPTION OF PREFERRED EMBODIMENTS

Figure 1A:
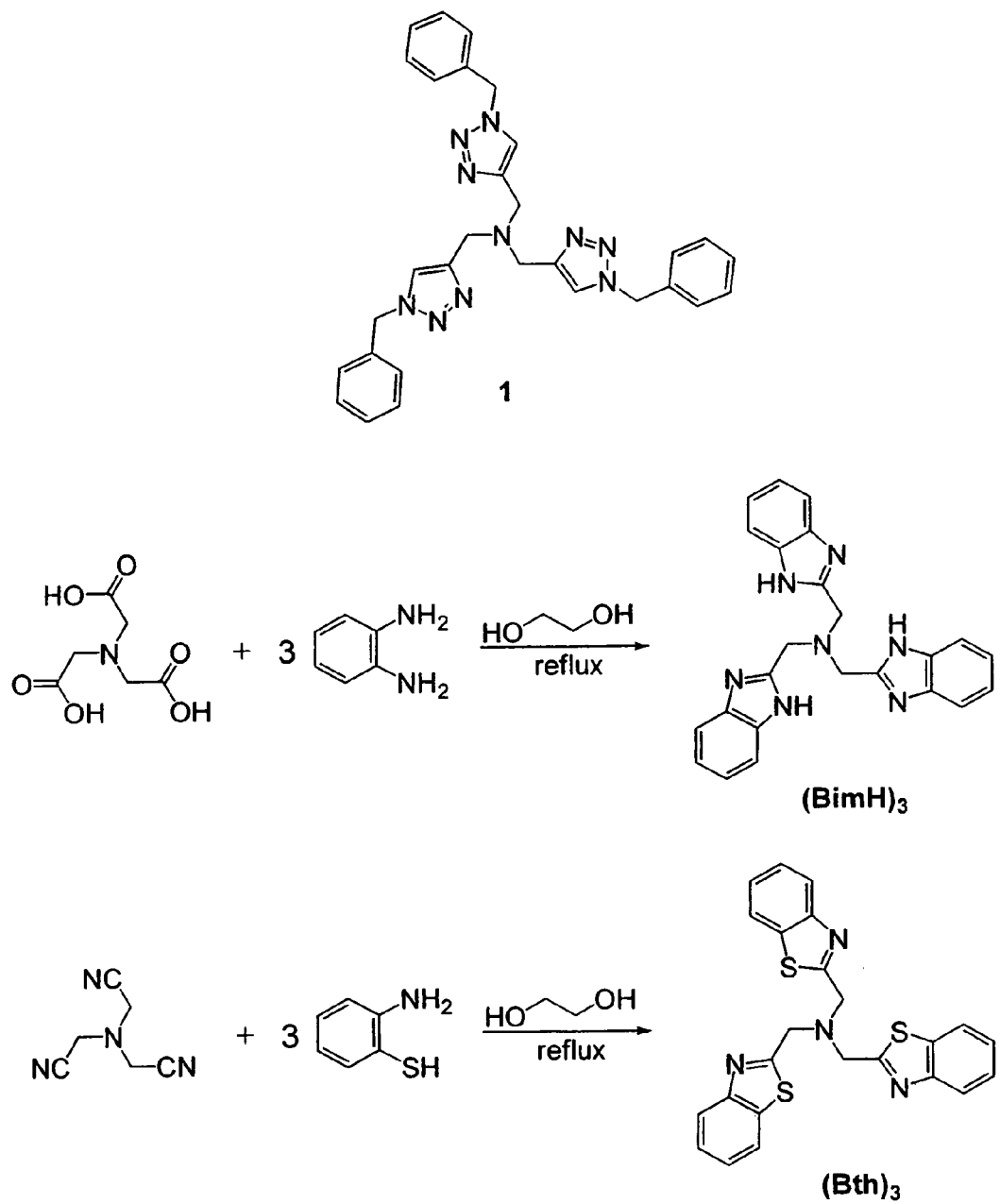
FIG. 1A illustrates the synthesis of tris(benzimidazole) and tris(benzothiazole) ligands.

The present invention provides ligands capable of complexing with metal ions such as copper, which are useful for promoting copper-catalyzed azide-alkyne cycloaddition reactions. A ligand of the invention comprises compound represented by structural Formula (I):

Formula (I)

wherein
$Z^1$ is a nitrogen-containing heterocyclic group or $Y^1$—$(CH_2)_c$—$Y^2$—$(CH_2)_d$—$Y^3$—$CH_2$—$N(CH_2Z^4)(CH_2Z^5)$;
$Y^1$ is -$E^1$-C(O)O—, -$E^1$-C(O)NH—, -$E^1$-, or a covalent bond;
$Y^2$ is a covalent bond, —CH=CH—, or a 1,4-(1,2,3-triazolyl) group;
$Y^3$ is —OC(O)-$E^2$-, —NHC(O)-$E^2$-, -$E^2$-, or a covalent bond;
each of $E^1$ and $E^2$ is a benzimidazolyl group attached at the 1 and 2 positions;
each of c and d is independently 1, 2, 3, 4, or 5;
each of $Z^2$, $Z^3$, $Z^4$ and $Z^5$ is a nitrogen-containing heterocyclic group;
each of the nitrogen-containing heterocyclic groups of the compound bears at least one substituent, $X^1$, and optionally bears a substituent, —$(CH_2)_n$—$R^1$;
each nitrogen containing heterocyclic group is independently selected from the group consisting of a 2-benzimidazolyl group, a 2-benzothiazolyl group, a 2-pyridyl group, a 2-oxazolinyl group, a 2-oxazolyl group, a 1-(1,2,3-triazolyl) group, a 4-(1,2,3-triazolyl) group, a 5-(1,2,3-triazolyl) group, and optionally an azoferrocenyl group;
each $X^1$ is independently selected from the group consisting of H, phenyl, benzyl, a halogen (e.g., chloro, bromo, or iodo), —$SO_3M$, —$SO_3H$, $C_1$-$C_6$-alkyl (e.g., methyl, ethyl, isopropyl, t-butyl, and the like), and $C_1$-$C_6$-alkoxy (e.g., methoxy, ethoxy, and the like);
each $R^1$ is independently selected from the group consisting of —C(O)OH, —C(O)OM, —C(O)$OR^2$, —C(O)$NHR^3$, and —C(O)$R^4$;
each M is an alkali metal ion (e.g., sodium or potassium) or ammonium ion;

each $R^2$ and $R^3$ is independently a $C_1$-$C_6$-alkyl group (e.g., methyl, ethyl, t-butyl, and the like);

each $R^4$ is independently H or a $C_1$-$C_6$-alkyl group (e.g., methyl, ethyl, and the like);

each n is independently 1, 2, 3, 4, 5, 6, 7, 8, 9, or 10;

with the provisos that:

when $Z^1$ is a nitrogen-containing heterocyclic group, and each heterocyclic group in the compound is a 2-benzimidazolyl group, and none of the 2-benzimidazolyl groups includes a —$(CH_2)_n$—$R^1$ substituent, then at least one of the 2-benzimidazolyl groups of the ligand also includes an $X^1$ substituent that is not H, —$SO_3M$, or —$SO_3H$; however, when at least one of the 2-benzimidazolyl groups includes a —$(CH_2)_n$—$R^1$ substituent, then at least one of the 2-benzimidazolyl groups also includes an $X^1$ substituent that is not H, or at least one other 2-benzimidazolyl group includes a —$(CH_2)$—$R^1$ substituent;

when $Z^1$ is a nitrogen-containing heterocyclic group, and each heterocyclic group in the compound is a 2-pyridyl group, then at least one of the 2-pyridyl groups includes an $X^1$ substituent that is not H; and when $Z^1$ is a nitrogen-containing heterocyclic group, and at least one of the heterocyclic groups is a 4-(1,2,3-triazolyl) group, then at least one other of the heterocyclic groups of the compound is not a 4-(1,2,3-triazolyl) group.

One preferred embodiment of a ligand of the present invention comprises a compound of Formula (I) in which $Z^1$ is a nitrogen-containing heterocyclic group. The compounds of this embodiment include a central tertiary amine surrounded by three nitrogen-containing heterocyclic groups each linked to the tertiary amine by a methylene group. The ligands encompassed by this preferred embodiment can alternatively be represented by structural Formula (II):

Formula (II)

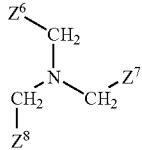

Figure 12:
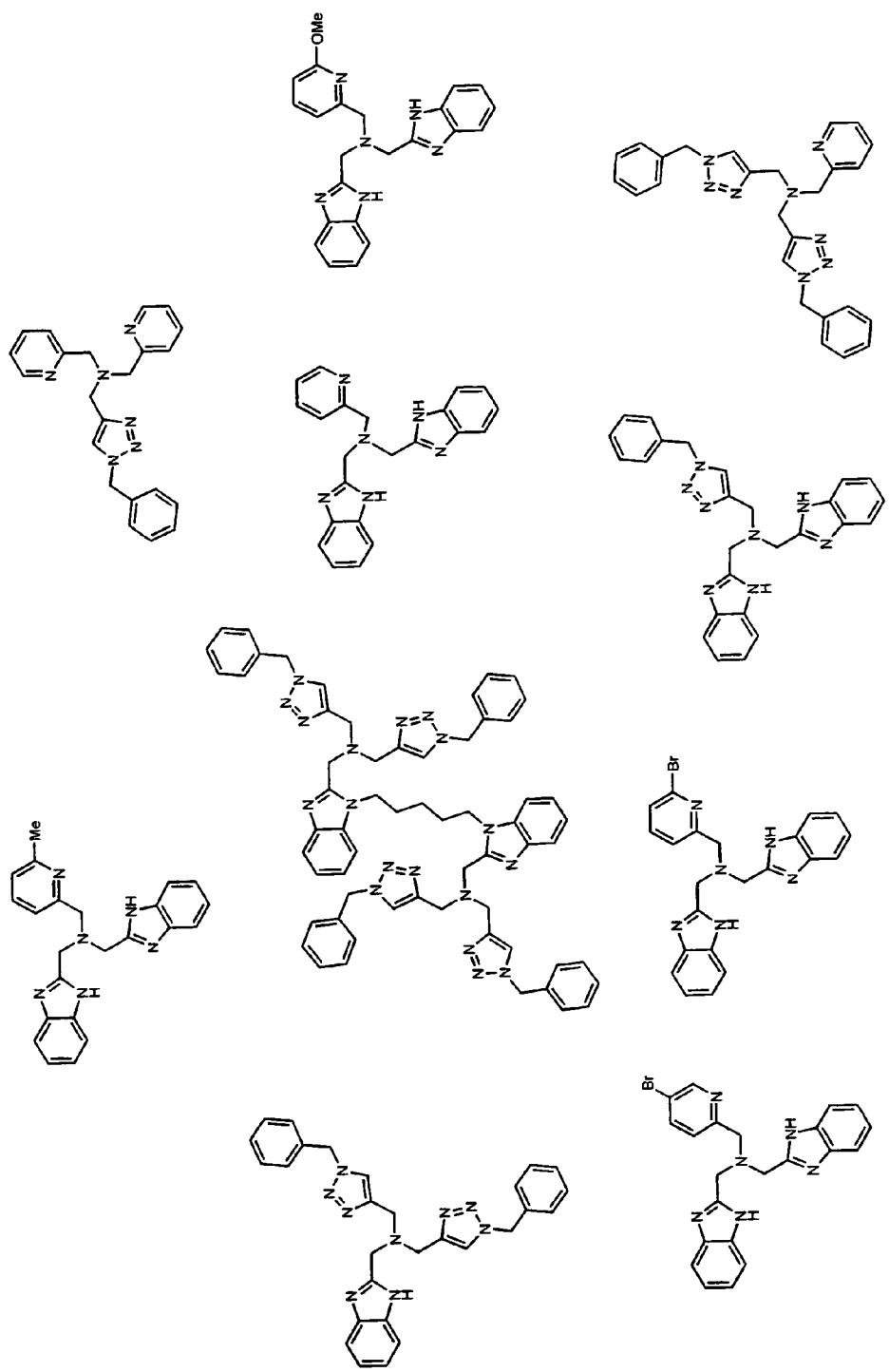
FIG. 12 illustrates additional ligands of the invention.
Figure 13:
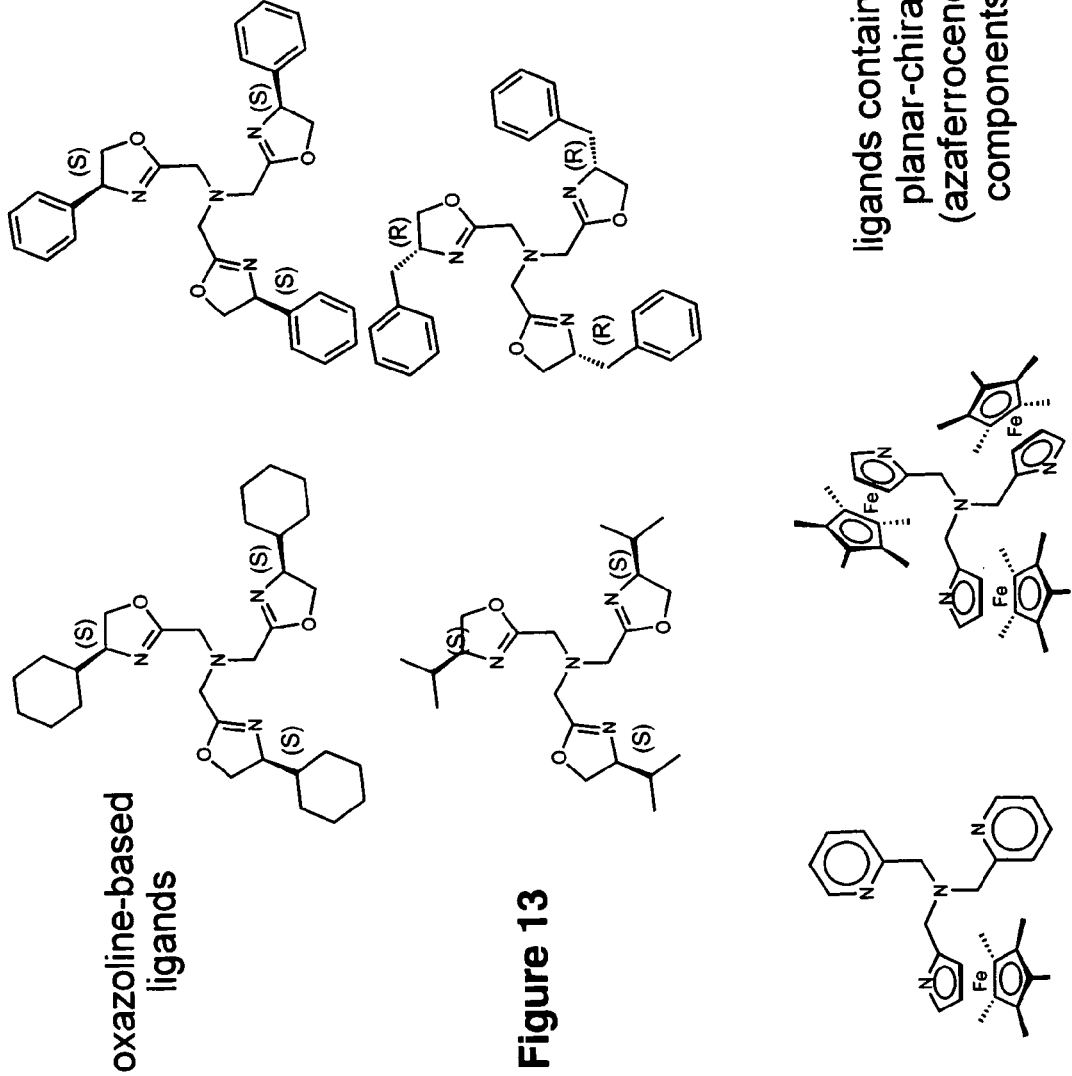
FIG. 13 illustrates additional ligands of the invention.

In Formula (II) each of $Z^6$, $Z^7$, and $Z^8$ is independently a nitrogen-containing heterocyclic group bearing at least one substituent, $X^2$, and optionally bears a substituent, —$(CH_2)_m$—$R^5$. Each of the nitrogen-containing heterocyclic groups of the compound is independently selected from the group consisting of a 2-benzimidazolyl group, a 2-benzothiazolyl group, a 2-pyridyl group, a 2-oxazolinyl group (e.g., as shown in FIG. 12), a 2-oxazolyl group, a 1-(1,2,3-triazolyl) group, a 4-(1,2,3-triazolyl) group, a 5-(1,2,3-triazolyl) group, and optionally an azoferrocenyl group (e.g., as shown in FIG. 13). Each $R^5$ is independently selected from the group consisting of —$C(O)OH$, —$C(O)OM$, —$C(O)OR^6$, —$C(O)NHR^7$, and —$C(O)R^8$. Each M is an alkali metal ion or ammonium ion. Preferably, M is a potassium ion or a sodium ion. Each $R^6$ and $R^7$ is independently a $C_1$-$C_6$-alkyl group (e.g., methyl, ethyl, or t-butyl), while each $R^8$ is independently H or a $C_1$-$C_6$-alkyl group (e.g., methoxy or ethoxy); and each m is independently 1, 2, 3, 4, 5, 6, 7, 8, 9, or 10 (preferably 3, 4, or 5). Ligands in which one or more of the heterocyclic groups is a 2-oxazolinyl group preferably include a chiral center at the 5-position of the heterocyclic ring (e.g., as illustrated by compounds shown in FIG. 13).

In Formula (II), when each heterocyclic group in the compound is a 2-benzimidazolyl group, and none of the 2-benz-imidazolyl groups includes a —$(CH_2)_m$—$R^5$ substituent, then at least one of the 2-benzimidazolyl groups of the ligand also includes an $X^2$ substituent that is not H, —$SO_3M$, or —$SO_3H$. In this embodiment, when at least one of the 2-benzimidazolyl groups includes a —$(CH_2)_n$—$R^5$ substituent, then at least one of the 2-benzimidazolyl groups also includes an $X^2$ substituent that is not H, or at least one other 2-benzimidazolyl group includes a —$(CH_2)_m$—$R^5$ substituent. When each heterocyclic group in Formula (II) is a 2-pyridyl group, then at least one of the 2-pyridyl groups includes an $X^2$ substituent that is not H. When at least one of the heterocyclic groups is a 4-(1,2,3-triazolyl) group, then at least one other of the heterocyclic groups of Formula (II) is not a 4-(1,2,3-triazolyl) group.

In some preferred embodiments of Formula (II), each heterocyclic group is a benzimidazolyl group. In other preferred embodiments, each heterocyclic group is a benzothiazolyl group. In yet other preferred embodiments, at least one of the heterocyclic groups is a benzimidazolyl group, and the other heterocyclic groups are independently selected from the group consisting of 2-benzothiazolyl, 2-pyridyl, and 4-(1,2, 3-triazolyl). In particularly preferred embodiments, at least one of the heterocyclic groups is a benzimidazolyl group bearing a —$(CH_2)_m$—$R^5$ substituent at N1 of the benzimidazolyl group, wherein $R^5$ is independently of —$C(O)OH$, —$C(O)OM$, or —$C(O)OR^6$; M is potassium or sodium, $R^6$ is methyl, ethyl, or t-butyl; and m preferably is 3, 4, or 5.

Another preferred embodiment of a ligand of the present invention comprises compounds of Formula (I) wherein $Z^1$ is $Y^1$—$(CH_2)_c$—$Y^2$—$(CH_2)_d$—$Y^3$—$N(CH_2Z^4)(CH_2Z^5)$, as defined hereinabove. The compounds of this embodiment comprise two tethered tertiary amines in which each of the tertiary amines is bound to two nitrogen-containing heterocyclic groups via methylene linkages. The compounds of this preferred embodiment of the present invention can alternatively be represented by structural Formula (III):

Formula (III)

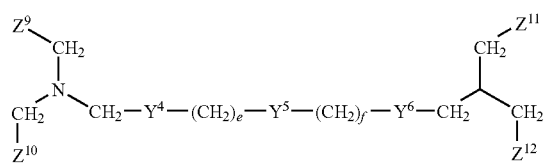

In Formula (III), $Y^4$ is -$E^3$-$C(O)O$—, -$E^3$-$C(O)NH$—, -$E^3$-, or a covalent bond; $Y^5$ is a covalent bond, —$CH$=$CH$—, or a 1,4-(1,2,3-triazolyl) group; $Y^6$ is —$OC(O)$-$E^4$-, —$NHC(O)$-$E^4$-, -$E^4$-, or a covalent bond; each of $E^3$ and $E^4$ is a benzimidazolyl group attached at the 1 and L, and $Z^{12}$ is a nitrogen-containing heterocyclic group bearing at least one substituent, $X^3$, and optionally bears a substituent, —$(CH_2)_p$—$R^9$. Each nitrogen containing heterocyclic group is independently selected from the group consisting of a 2-benzimidazolyl group, a 2-benzothiazolyl group, a 2-pyridyl group, a 2-oxazolinyl group, a 2-oxazolyl group, a 1-(1, 2,3-triazolyl) group, a 4-(1,2,3-triazolyl) group, a 5-(1,2,3-triazolyl) group, and optionally an azoferrocenyl group. Each $X^3$ is independently selected from the group consisting of H, phenyl, benzyl, a halogen (e.g., chloro, bromo, or iodo), —$SO_3M$, —$SO_3H$, $C_1$-$C_6$-alkyl (e.g., methyl, ethyl, isopropyl, t-butyl, and the like), and $C_1$-$C_6$-alkoxy (e.g., methoxy, ethoxy, and the like). Each $R^9$ is independently selected from the group consisting of —$C(O)OH$, —$C(O)OM$, —$C(O)OR^{10}$, —$C(O)NHR^{11}$, and —$C(O)R^{12}$; each M is an alkali metal ion (e.g., sodium or potassium) or ammonium ion; each $R^{10}$ and $R^{11}$ is independently a $C_1$-$C_6$-alkyl group (e.g., methyl, ethyl, t-butyl, and the like); each $R^{12}$ is independently H or a $C_1$-$C_6$-alkyl group (e.g., methyl, ethyl, and the like); and each p is independently 1, 2, 3, 4, 5, 6, 7, 8, 9, or 10 (preferably 3, 4, or 5).

In some preferred embodiments of Formula (III), at least one, and preferably at least two, of the heterocyclic groups is a 2-benzimidazolyl group. In other preferred embodiments $Z^9$ and $Z^{11}$ are identical to one another (e.g., both being 2-benzimidazolyl groups having the same $X^3$ substituents), and $Z^{10}$ and $Z^{12}$ are identical to one another (e.g., both being 2-benzimidazolyl groups, both being 2-pyridyl groups, or both being 4-(1,2,3-triazolyl) groups, and each having with the same $X^3$ and —$(CH_2)_p$—$R^9$ substituents).

One preferred class of ligands encompassed by Formulas (I) and (II) is alternatively represented by structural Formula (IV):

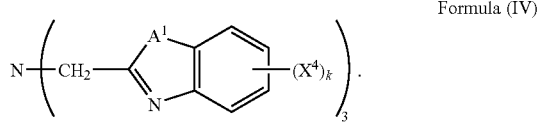

Formula (IV)

In Formula (IV), each $X^4$ is independently selected from the group consisting of H, phenyl, benzyl, a halogen (e.g., chloro or bromo), —$SO_3M$, —$SO_3H$, $C_1$-$C_6$-alkyl (e.g., methyl or ethyl), and $C_1$-$C_6$-alkoxy (e.g., methoxy or ethoxy), and k is 1 or 2. Each $A^1$ is independently selected from the group consisting of S and N—$R^{13}$, where each $R^{13}$ is independently selected from the group consisting of hydrogen, $C_1$-$C_6$-alkyl (e.g., methyl of ethyl), and —$(CH_2)_r$—$R^{14}$, where r is an integer in the range of 1 to 10 (preferably 3, 5, or 5), and each $R^{14}$ is independently selected from the group consisting —$C(O)OH$, —$C(O)OM$, —$C(O)OR^{15}$, —$C(O)NHR^{16}$, and —$C(O)R^{17}$. Each M is an alkali metal ion (e.g., potassium or sodium) or ammonium ion. Each $R^{15}$ and $R^{16}$ is independently a $C_1$-$C_6$-alkyl group (e.g., methyl, ethyl, or t-butyl). Each $R^{17}$ is independently H or a $C_1$-$C_6$-alkyl group (e.g., methyl or ethyl). However, the following proviso applies to compounds of Formula (IV): if each $A^1$ is NH, then at least one $X^4$ is not H. In a preferred embodiment, each $A^1$ is independently N—$R^{13}$. In another preferred embodiment, each $R^{13}$ is independently —$(CH_2)_r$—$R^{14}$. In yet another preferred embodiment, each $R^{13}$ is independently selected from the group consisting of the following structures:

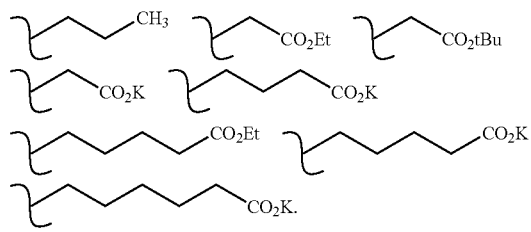

Another preferred class of ligands encompassed by Formulas (I) and (II) is alternatively represented by structural Formula (V):

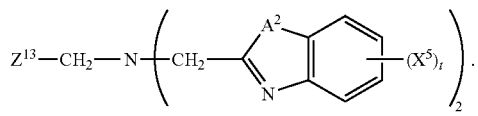

Formula (V)

In Formula (V), each $X^5$ is independently selected from the group consisting of H, phenyl, benzyl, a halogen (e.g., chloro or bromo), —$SO_3M$, —$SO_3H$, $C_1$-$C_6$-alkyl (e.g., methyl or ethyl), and $C_1$-$C_6$-alkoxy (e.g., methoxy or ethoxy), and t is 1 or 2. Each $A^2$ is independently selected from the group consisting of S and N—$R^{18}$, where each $R^{18}$ is independently selected from the group consisting of hydrogen, $C_1$-$C_6$-alkyl (e.g., methyl of ethyl), and —$(CH_2)_x$—$R^{19}$, where x is an integer in the range of 1 to 10 (preferably 3, 5, or 5), and each $R^{19}$ is independently selected from the group consisting —$C(O)OH$, —$C(O)OM$, —$C(O)OR^{20}$, —$C(O)NHR^{21}$, and —$C(O)R^{22}$. Each M is an alkali metal ion (e.g., potassium or sodium) or ammonium ion. Each $R^{20}$ and $R^{21}$ is independently a $C_1$-$C_6$-alkyl group (e.g., methyl, ethyl, or t-butyl). Each $R^{22}$ is independently H or a $C_1$-$C_6$-alkyl group (e.g., methyl or ethyl). $Z^{13}$ is a heterocyclic group bearing at least one substituent, $X^6$, wherein each heterocyclic group is independently selected from the group consisting of 2-pyridyl, 4-(1,2,3-triazolyl), and optionally azoferrocenyl. Each $X^6$ is independently selected from the group consisting of H, phenyl, benzyl, a halogen (e.g., chloro or bromo), —$SO_3M$, —$SO_3H$, $C_1$-$C_6$-alkyl (e.g., methyl or ethyl), and $C_1$-$C_6$-alkoxy (e.g., methoxy or ethoxy).

Another preferred class of ligands encompassed by Formulas (I) and (II) is alternatively represented by structural Formula (VI):

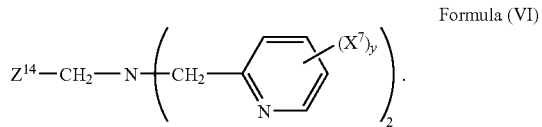

Formula (VI)

In Formula (VI), y is 1 or 2; and each $X^7$ is independently selected from the group consisting of H, phenyl, benzyl, a halogen (e.g., chloro or bromo), —$SO_3M$, —$SO_3H$, $C_1$-$C_6$-alkyl (e.g., methyl or ethyl), and $C_1$-$C_6$-alkoxy (e.g., methoxy or ethoxy), and y is 1 or 2. $Z^{14}$ is a heterocyclic group bearing at least one substituent, $X^8$, wherein each heterocyclic group is independently selected from the group consisting of 2-benzimidazolyl, 2-benzothiazolyl, 2-pyridyl, 4-(1,2,3-triazolyl), and optionally azoferrocenyl. Each $X^8$ is independently selected from the group consisting of H, phenyl, benzyl, a halogen (e.g., chloro or bromo), —$SO_3M$, —$SO_3H$, $C_1$-$C_6$-alkyl (e.g., methyl or ethyl), and $C_1$-$C_6$-alkoxy (e.g., methoxy or ethoxy). When $Z^{14}$ is a 2-benzimiazolyl group, the 2-benzimiazolyl group optionally includes a substituent —$(CH_2)_z$—$R^{23}$ at N1 of the 2-benzimidazolyl group, and z is 1, 2, 3, 4, 5, 6, 7, 8, 9, or 10 (preferably 3, 4, or 5). $R^{23}$ is selected from the group consisting —$C(O)OH$, —$C(O)OM$, —$C(O)OR^{24}$, —$C(O)NHR^{25}$, and —$C(O)R^{26}$ (preferably $R^{23}$ is —$C(O)OH$, —$C(O)OM$, or —$C(O)OR^{25}$). Each M is an alkali metal ion (e.g., potassium or sodium) or ammonium ion. Each $R^{24}$ and $R^{25}$ is independently a $C_1$-$C_6$-alkyl group (e.g., methyl, ethyl, or t-butyl). Each $R^{26}$ is independently H or a $C_1$-$C_6$-alkyl group (e.g., methyl or ethyl).

Figure 1B:
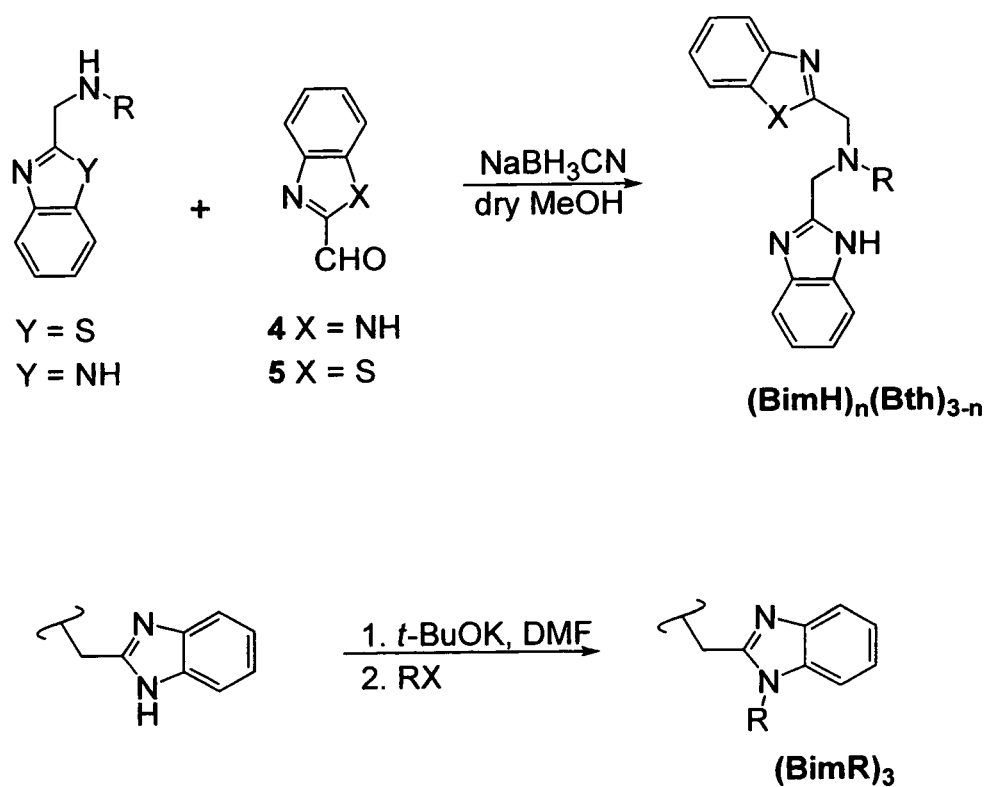
FIG. 1B illustrates the synthesis of mixed heterocycle and alkylated benzimidazole variants.

Some preferred ligands of Formulas (I), (II), (III), (IV), (V) and (VI) are shown in FIG. 1C, and in FIGS. 10, 11, 12, and 13. FIG. 1 also depicts certain comparative ligands such as (BimH)$_3$, (BimH/S)$_3$, (Py)$_3$, Py(BimC$_4$A)$_2$, H(BimH)$_2$, H(Bth)$_2$, (BimH)$_2$C$_2$(BimH)$_2$, Compound 2, and Compound 3. All abbreviations used herein to refer to the ligands are shown in FIG. 1C. As used herein, the ligand abbreviations in the specification and in FIG. 1C are constructed a follows: For compounds having three heterocyclic groups surrounding a single central tertiary amine, abbreviations for the heterocyclic groups surrounding a core structure of N(CH$_2$—)$_3$ are shown in the parentheses, where BimH stands for an unsubstituted 2-benzimiadolyl group, Bth stands for a 2-benzothiazolyl group, and Py stands for a 2-pyridyl group. N-substituted 2-benzothiazolyl groups are designated a BimC$_x$R where C$_x$R designates a —(CH$_2$)$_x$R group on the N1 nitrogen of the 2-benzimiazolyl group, where x denotes the number of methylene groups (CH$_2$) and R is a functional group selected from is H, E, E', or A (E=CO$_2$-Et; E'=CO$_2$-tBu, and A=CO$_2^-$ K$^+$). A "/S" designation after the "Bim" abbreviation stands for a 5-sulfonate-substituted 2-benzimidazolyl group and a "/Me$_2$" designation after the "Bim" abbreviation stands for a 5,6-dimethyl-substituted 2-benzimidazolyl group. Compounds having only 2 groups within parentheses denote comparative ligands with only two-heterocyclic groups bound to an amino group via methylene links, thus H(BimH)$_2$ refers to HN(CH$_2$-(2-benzimidazolyl))$_2$. For compounds having two tertiary amino groups linked by a bridging alkylene group, such as (BimH)$_2$C$_2$(BimH)$_2$, the groups in parentheses have the same meanings as described above, each linked by a CH$_2$ group to a tertiary amine, and the alkylene bridge between two tertiary amino groups is designated C$_y$, which refers to a chain of "y" methylene units, thus (BimH)$_2$C$_2$(BimH)$_2$ refers to ((2-benzimidazolyl)CH$_2$)$_2$NCH$_2$CH$_2$N(CH$_2$-(2-benzimidazolyl))$_2$.

Ligand Synthesis.

Tris(2-benzimidazolylmethyl)amine, designated (BimH)$_3$, was prepared by the condensation of 1,2-phenylenediamine with nitrilotriacetic acid. A variety of X-ray crystal structures of metal complexes involving this type of ligand have been reported (Blackman, A. G. *Polyhedron* 2004, 24, 1-39), including Cu(I) and Cu(II) complexes of the N-propyl derivative (BimC$_3$H)$_3$ (Su, C.-Y.; et al. *Polyhedron* 1999, 18, 1577-1585). (See FIG. 1C for structures of various ligands discussed herein and the abbreviations used to refer to the ligands).

Tris- and bis-(benzothiazole)amines (Bth)$_3$ and H(Bth)$_2$ (FIG. 1) were obtained by the condensation of 1,2-aminothiophenol with nitrilotriacetonitrile and iminodiacetonitrile, respectively. Mixed benzimidazole/benzothiazole ligands (BimH)$_2$(Bth) and (BimH)(Bth)$_2$ were prepared by reductive amination reactions between secondary amines H(BimH)$_2$ and H(Bth)$_2$ and the corresponding heterocyclic aldehydes, as shown in FIG. 1. Among the tripodal structures, (Bth)$_3$ and (BimC$_1$H)$_3$ have unusually low solubility in common organic solvents, including DMSO.

(BimR)$_3$ derivatives were prepared to evaluate the effects of heterocyclic N-substitution on catalytic activity and water solubility. Alkylation with methyl, ethylacetyl, and tert-butylacetyl groups provided the neutral ligands (BimC$_1$H)$_3$, (BimC$_1$E)$_3$, and (BimC$_1$E')$_3$, respectively; ester hydrolysis provided the water-soluble analogue (BimC$_1$A)$_3$. Longer-chain analogs were made similarly, with (BimC$_n$A)$_3$ (with 3, 4, or 5 methylene units) ligands were somewhat water soluble and detergent-like at higher concentrations. Ligands (BimH/S)$_3$ and (BimH/Me$_2$)$_3$ provided alternatives that are much more hydrophilic and mildly more hydrophobic and electron-rich, respectively.

The counter ions for the carboxylic and sulfonic acid functional groups were chosen so that they would not interfere with the function of the copper ligand. Simple counter ions such as alkali metal ions (e.g., K or Na) or ammonium ions are preferred as they do not cause aggregation or precipitation of the catalyst during the CuAAC reaction.

Kinetic Comparisons

The relative effectiveness of Cu-ligand complexes was evaluated on the reaction between phenylacetylene and benzyl azide in 4:1 DMSO:aqueous buffer containing sodium ascorbate as reducing agent, which has served as the standard reaction in previous mechanistic studies (Rodionov, V. O.; et al. *Angew. Chem. Int. Ed.* 2005, 44, 2210-2215). Ligand:Cu ratios are used herein to describe the amounts of each component added, and designate mixtures of ligands and copper ions according to those ratios for convenience. However, it must be emphasized that the active catalysts are not necessarily composed of those same ratios of ligand and metal as are placed in the reaction vessel. The equilibria that govern the composition of these catalysts are discussed below, and their study will be the subject of a separate publication.

Absolute rates were determined under relatively dilute conditions (1-2 mM in substrates), which were required to slow the reactions enough so that aliquots could be reliably taken over a substantial fraction of the completion curve. Each aliquot was immediately quenched and the amount of product formed monitored by quantitative LC-MS against an internal standard. In this way, the clean conversion to triazole was verified in each case, information that is not available by following the disappearance of azide or alkyne by infrared spectroscopy. Plots of product concentrations vs. time fitted very well to second-order kinetics over at least 70% of the reaction (FIG. 2A). A ligand:metal ratio of 2:1 was found to be optimal for TBTA (1) by this method, which matches the results from previous work on other ligands (Lewis, W. G.; et al. *J. Am. Chem. Soc.* 2004, 126, 9152-9153). For this reason, comparisons were made between second-order specific activities (rate constants determined at a standard Cu concentration of 0.1 mM) for catalysts composed of 2:1 mixtures of ligands and Cu(I), in the presence of excess ascorbate relative to Cu.

In general, benzimidazole-based ligands provided for faster reactions than the tris(triazolyl) structure 1 (also referred to as TBTA), and in the same range as the previously identified sulfonated bathophenanthroline 2 (Lewis, W. G.; et al. *J. Am. Chem. Soc.* 2004, 126, 9152-9153). The magnitude of ligand accelerated catalysis (ratio of the observed rates in the presence vs. the absence of added ligand) was substantial (more than an order of magnitude). It is also apparent that reaction rate is sensitive to both the nature of the heterocycle and to substitution on the benzimidazole ring. The replacement of benzimidazoles with benzothiazoles in the N(CH$_2$heterocycle) format gave no appreciable loss in catalyst efficiency, as long as at least one benzimidazole side arm was present. (Bth)$_2$(BimH) was found to be the best ligand in the series, with rates following the order (Bth)$_3$<<(Bth) (BimH)$_2$<(BimH)$_3$<<(Bth)$_2$(BimH). N-Substitution of the tris(benzimidazole) ligand was extensively investigated, with small pendant alkyl and ester groups ((BimC$_1$E)$_3$, (BimC$_1$E')$_3$, (BimC$_1$H)$_3$) performing as well as the parent structure (BimH)$_3$. The installation of pendant carboxylic acid groups gave rise to noticeably better catalyst performance in case of longer chain lengths e.g., (BimC$_4$A)$_3$, (BimC$_4$A/Me$_2$)$_3$, (BimH)(BimC$_5$A)$_2$, (BimC$_3$A)$_3$, (BimC$_5$A)$_3$. The ester (BimC$_4$E)$_3$ was just as active as its hydrolyzed (carboxylate) analog. In contrast, (BimC$_1$A)$_3$ which features carboxylic acid groups separated from the benzimidazole core by just one carbon atom, produced one of the least effective catalysts in the series, much less effective than its ester (BimC$_3$E)$_3$.

Some indications of the response of the process to changes in pH and to the presence of added buffer salts are provided by FIGS. 2C and 2D. In absence of catalytic ligands, preparative CuAAC reactions at the bench are remarkably tolerant of large changes in pH: only highly acidic conditions (pH 2 or lower) can halt the reaction, possibly by affecting Cu speciation or inhibiting the formation of Cu-acetylides. In general, more basic conditions promote the reaction, and this trend is also evident in the absolute rates measured for several added ligands, as shown in FIG. 2C. However, different Cu-ligand catalysts respond differently. For example, the mixed benzimidazole/benzothiazole system (Bth)$_2$(BimH) showed very little change in rate when the pH of the aqueous component of the solvent mixture was raised from 7 to 8, whereas the parent tripodal ligands (Bth)$_3$ and (BimH)$_3$ were more sensitive.

The effects of pH prompted investigation of added buffer salts, even though excess ascorbate functions as a low-capacity buffer under the standard reaction conditions. The nature of the buffer was also found to have an impact on the CuAAC reaction. For example, while pH 8 Tris-HCl buffer has been successfully used for bioconjugation applications, reactions catalyzed by Cu.1 and Cu.(BimH)$_3$ mixtures in 4:1 DMSO: buffer are slowed significantly in the presence of Tris buffer over a standard range of concentrations, with the inhibitory effect being significantly more pronounced for 1. Another popular buffer system is based on HEPES (4-(2-hydroxyethyl)-1-piperazineethanesulfonic acid), which is known to have moderate affinity for Cu(II). HEPES buffer has little effect on the catalytic rate of a wide variety of Cu-ligand complexes at moderate concentrations (<100 mM, data not shown) for CuAAC reactions. Accordingly, HEPES (at 100 mM or less) is a preferred buffer whenever CuAAC reactions need to be performed at controlled moderate pH values in an aqueous environment. However, the use of a higher buffer concentration (180 mM) gave rise to the varying results shown in FIG. 2D. Three catalysts were found to give faster turnover in the presence of HEPES, with the effect being especially dramatic for Cu.(Bth)$_2$(BimH). Other catalysts bearing pendant carboxylate arms were found to be inhibited by 180 mM HEPES.

Figure 2:
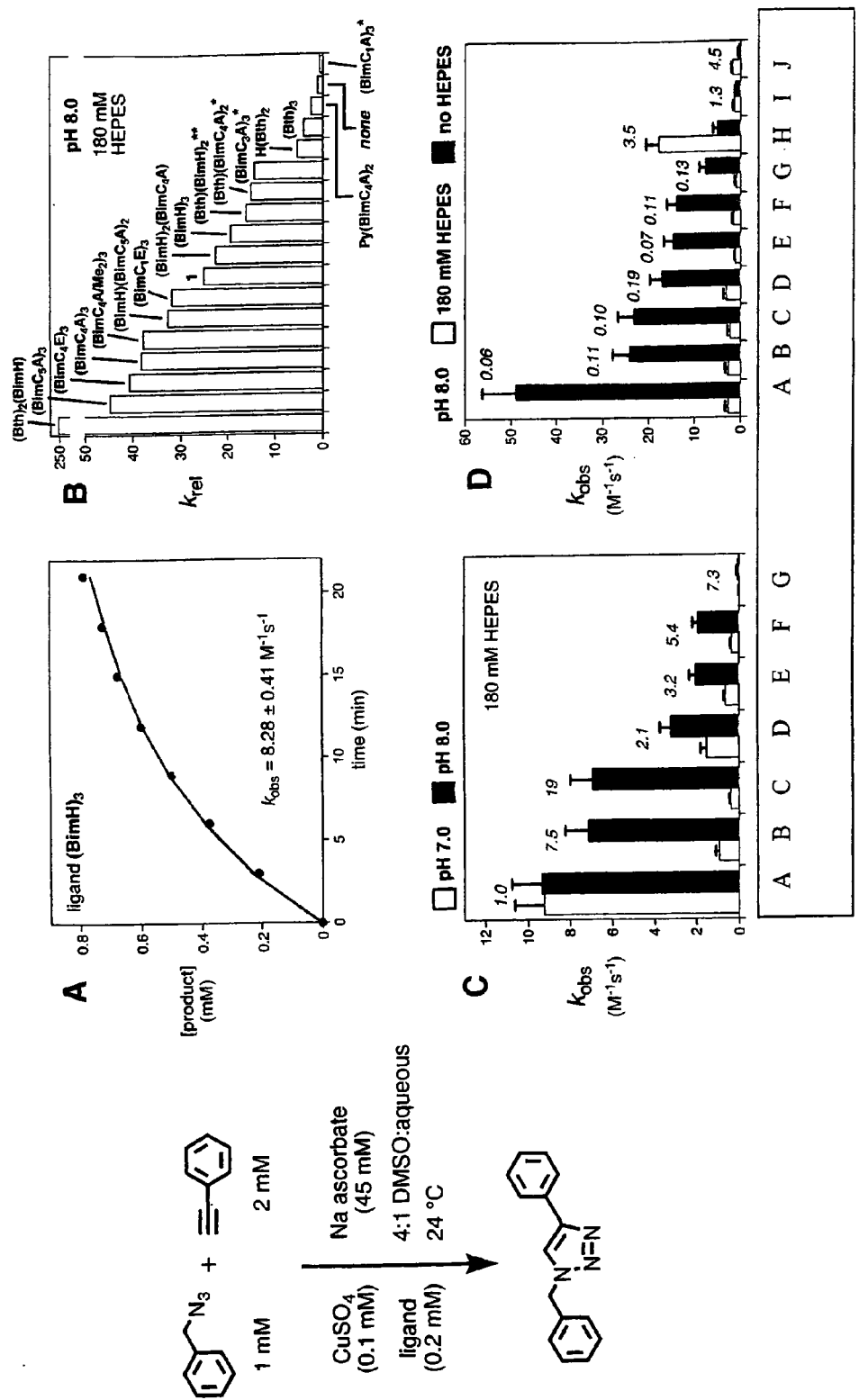
FIG. 2 illustrates a series of graphs of product concentration and rate constants, as well as a scheme of the reaction between benzyl azide and phenylacetylene a ligand in the presence of copper and reducing agent (sodium ascorbate). In Panel C, entries A, B, C, D, E, F, and G are $(Bth)_2(BimH)$, $(BimH)_3$, $(BimH/S)_3$, $(BimC_4A)_3$, $H(Bth)_2$, $(Bth)_3$, and $H(BimH)_2$, respectively. In Panel D, entries A, B, C, D, E, F, G, H, I and J are $(BimC_4E)_3$, $(BimC_4A)_3$, $(BimH)(BimC_5A)$, $(BimC_5A)_3$, $(Bth)(BimC_4A)_2$, $(BimH)_2(BimC_4A)$, $(BimC_3A)_3$, $(Bth)_2(BimH)$, $(BimH)_3$, and TBTA (1), respectively.

FIG. 2B also shows a small number of ligands that are either inhibitory or inconsequential relative to the rate of the "ligand-free" case. Thus, tris(pyridylmethyl)amine (Py)$_3$, secondary amine H(BimH)$_2$, and a ligand having heterocycles flanking a central pyridine motif (e.g., Py(BimC$_4$A)$_2$) each provided rates that were slower than those observed for the "ligand-free" case. Pybox derivative 3, previously used for kinetic resolution of racemic diazides (Meng, J.-C.; et al. Tetrahedron Lett. 2005, 46, 4543-4546), does not accelerate the reaction. We believe that these systems do not allow access to the correct coordination geometry to promote the reaction. The spectrum of results shown in FIG. 2 suggest that the response of various Cu.ligand catalysts to changes in pH and added coordinating ions is complex, and is likely to involve ligand-dependent changes in speciation, structure, and, perhaps, rate-limiting step of the catalytic cycle. From a practical perspective, (BimC$_4$A) and (BimH/S)$_3$ are attractive because they provide strong rate acceleration through a wide pH range and are soluble in water to at least 50 mM for the potassium salts, thus allowing for easy workup (see below).

Reaction Calorimetry.

Reaction calorimetry was used to evaluate the relative merits of various ligands under practical conditions of organic synthesis, e.g., involving high concentrations of azide and alkyne reagents and low loadings of catalyst. After correction for instrumental heat transfer parameters, thermograms provide a direct real-time measure of reaction rate (power output); integration gives the overall time-vs.-completion curve. Peak reaction exotherms proved to be a reproducible and convenient measurement of relative catalytic activity. All such measurements were made in the same 4:1 DMSO:aqueous solvent as before, but at 65° C. rather than room temperature, in order to keep the product triazole in solution at the higher concentrations used.

Figure 3:
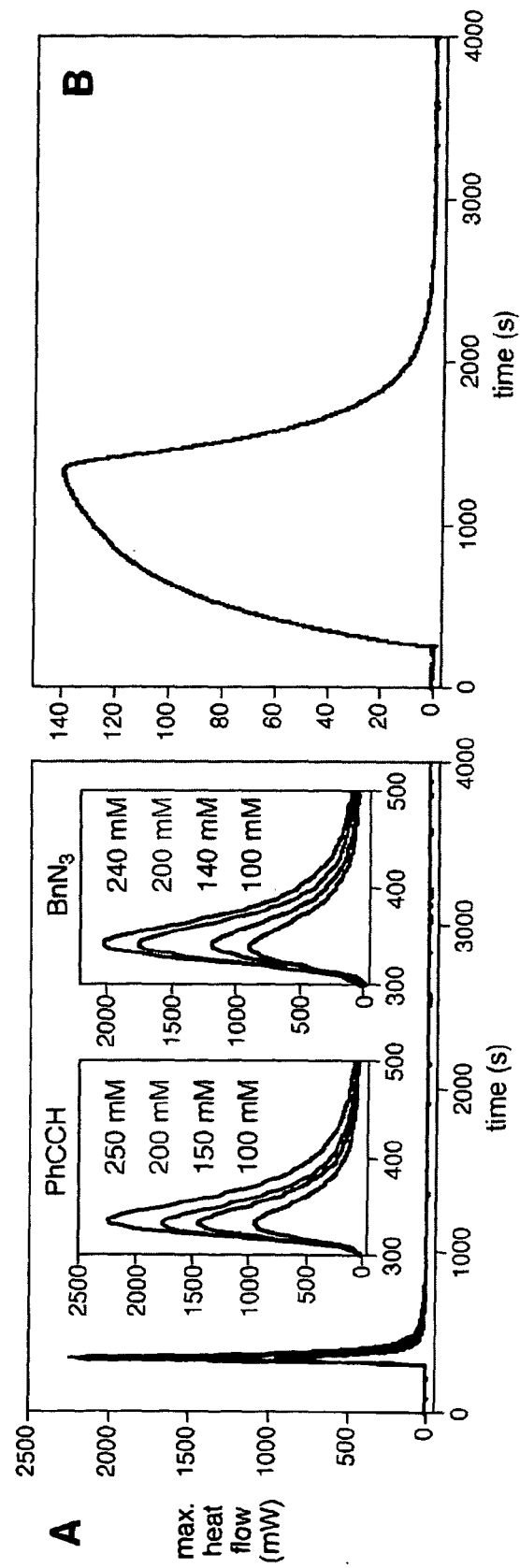
FIG. 3 illustrates two graphs of calorimetry data for the reaction of benzyl azide with phenylacetylene in the presence of $CuSO_4$.

Most ligands provided a clean profile characteristic of a second-order reaction involving a single catalyst species, as shown in FIG. 3A. TBTA (1) was an important exception, showing a markedly more gradual approach to a peak rate followed by a rapid drop to give the "sawtooth" thermogram shown in FIG. 3B. This reaction profile made direct calorimetric comparison between 1 and other ligands impossible; however, the peak power and integrated area indicated that compound 1 afforded a sluggish catalyst compared to many of the others tested (although still far more active than without ligand). Its unique thermogram suggests that changes in the Cu.1 catalyst composition occur as the reaction proceeds, since its profile does not correspond to typical kinetic expressions involving a single catalyst species. Two N-heterocyclic carbene complexes of Cu(I) were also tested, as a recent paper describing the use of this class of ligands has appeared (Díez-González, S.; et al. Chem. Eur. 12006, 12, 7558-7564). One of these ligands was inactive; the other performed approximately as well as 1, showing the same type of unusual rate-vs-time profile.

Figure 4:
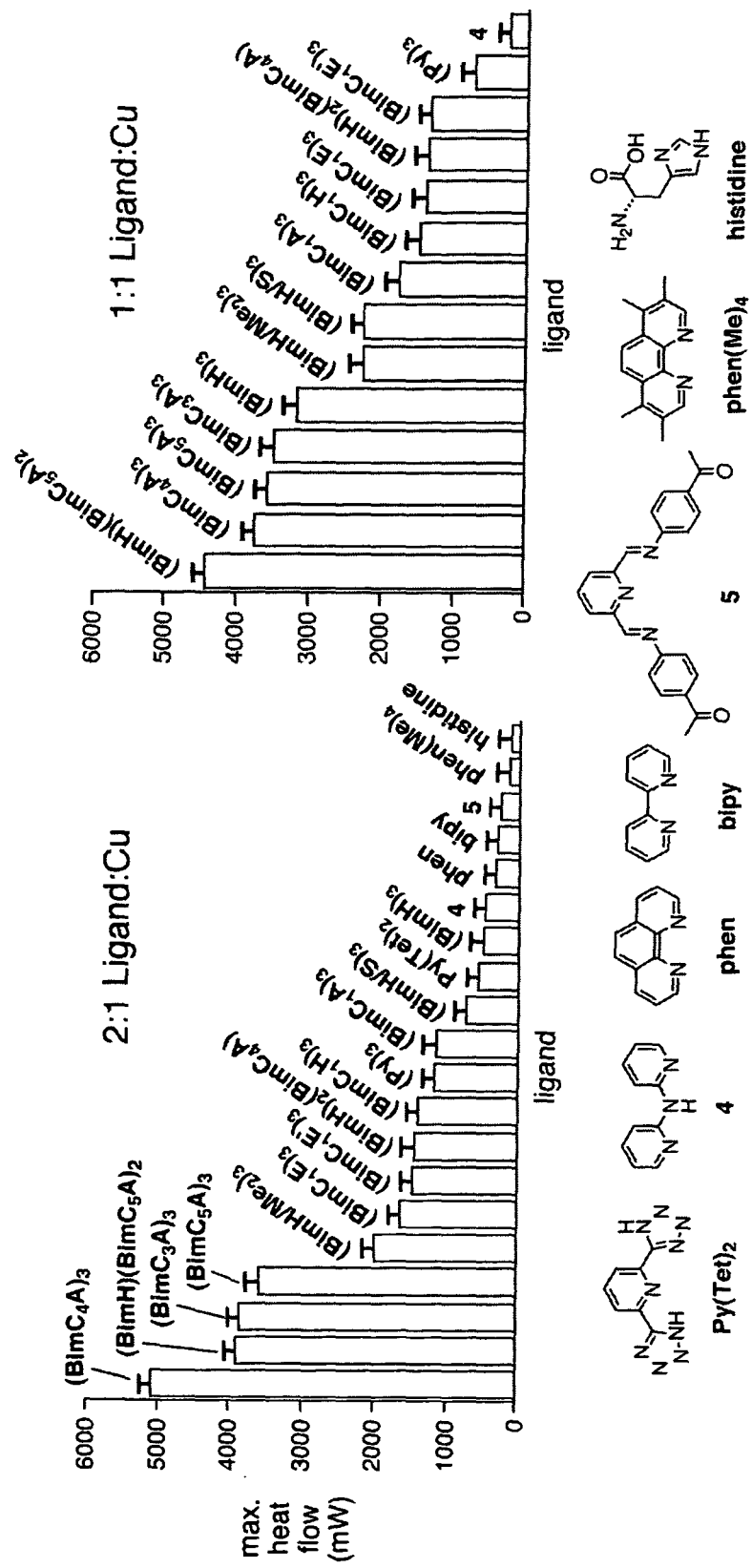
FIG. 4 illustrates two bar graphs of heat flow calorimetry data along with some structures of ligands used in the evaluation.

Approximately 100 ligands were tested by calorimetry at a ligand:Cu ratio of 2:1, and a subset of these were also evaluated at a 1:1 ratio. The results from the best systems are shown in FIG. 4. All the values in FIG. 4 represent substantial levels of ligand-accelerated catalysis, since the reaction without added ligand does not release enough heat to register on the calorimeter at all (although it does go to completion within 12 hours at 65° C.). All of the ligands in FIG. 4 show single-component "well behaved" kinetic characteristics (FIG. 3A). The ligand:metal ratio made little difference in the overall trends.

The results from calorimetry evaluations are largely consistent with the results obtained by analysis of quenched aliquots by LC-MS (FIG. 2). Both methods show tris(benzimidazole) derivatives to be excellent catalytic ligands, with those bearing longer alkylcarboxylate groups, i.e., (BimC$_4$A)$_3$, (BimH)(BimC$_5$A)$_2$, (BimC$_3$A)$_3$, and (BimC$_5$A)$_3$ being the best in the class. The ester (BimC$_4$E)$_3$ was not tested because ester hydrolysis can occur under the reaction conditions. The important exceptions are benzothiazole-containing ligands i.e., (Bth)$_3$, (Bth)$_2$(BimH), (Bth)(BimH)$_2$ and the tris (pyridylmethyl)amine ligand, (Py)$_3$. The former showed significant activity in the aliquot quenching screen (low reactant concentrations, 10% Cu), yet were largely inactive under calorimetry conditions (high reactant concentrations, 1% Cu). The opposite trend was observed for (Py)$_3$, which was one of the best ligands in calorimetry screening while performing poorly in aliquot quenching kinetics. These differences may be attributable to changes in copper speciation that are likely to accompany changes in overall reaction concentration and catalyst loading.

From a practical perspective, the tris(benzimidazole) family is an effective platform for catalysis of CuAAC reactions.

While not directly comparable due to the differences in rate profile described above, tris-triazole 1 ranks in the lower half of the ligands tested.

Figure 5:
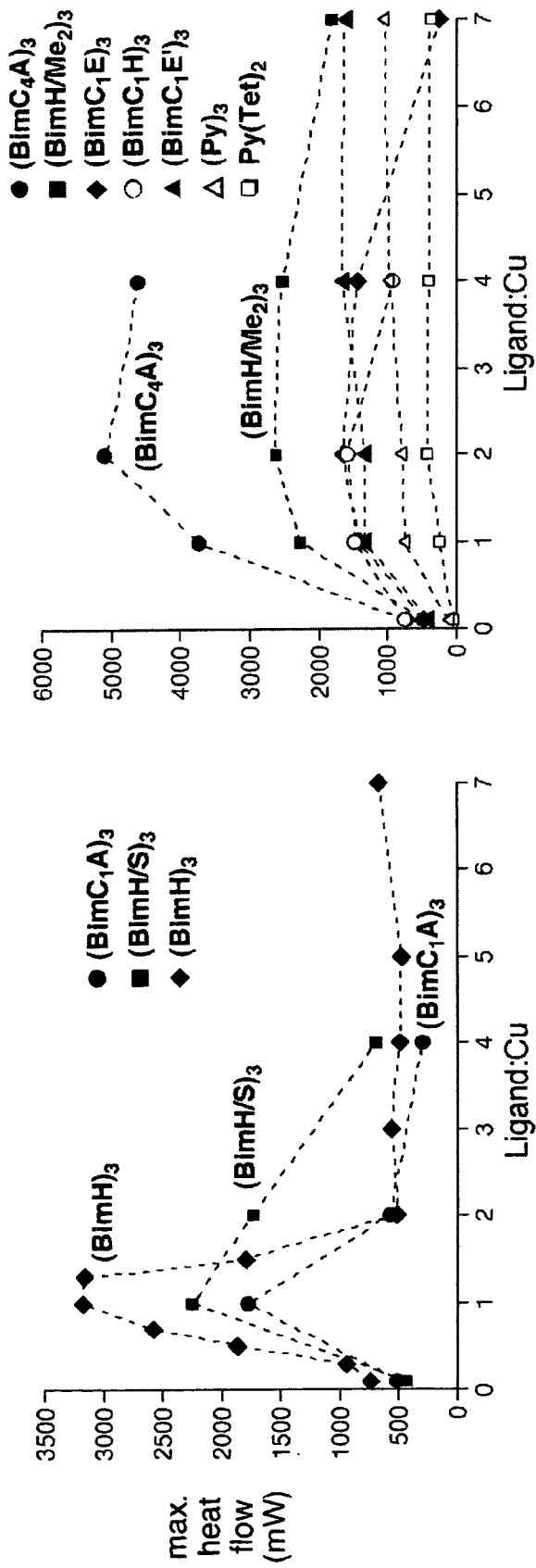
FIG. 5 illustrates two graphs showing dependence of the peak reaction power (peak rate) on ligand:Cu ratio for a subset of the best ligands identified in the initial screen.

A wider range of ligand:Cu ratios for some of the best ligands were also examined under concentrated conditions by calorimetry. These results, summarized in FIG. 5, show that the ligands may be divided into two categories—those that perform optimally at a 1:1 ratio (e.g., $(BimH)_3$, $(BimC_1A)_3$, $(BimH/S)_3$), and those that reach either a peak or a plateau at a 2:1 ratio (e.g., $(BimC_1H)_3$, $(BimC_1E)_3$, $(BimC_1E')_3$, $(BimC_4A)_3$, $(BimH/Me_2)_3$, $(Py)_3$, $Py(Tet)_2$). In most of the latter cases, the reaction was not dramatically slowed by the addition of excess ligand (4 or 7 equivalents). Even when a pronounced peak in activity was observed at an equimolar ligand:Cu ratio (e.g., $(BimH)_3$, $(BimC_1A)_3$, the reaction proceeded at a significant rate in the presence of excess ligand. This type of behavior is not normally exhibited by systems having a single active catalyst, the concentration of which is governed by a simple set of equilibria such as shown in Eq 1.

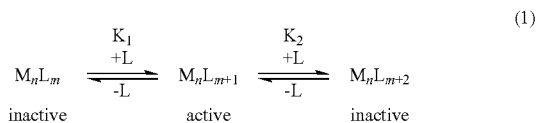

(1)

In situations such as Eq. 1, ligand-accelerated reactivity derives from the catalytic power of a complex containing a greater ligand:metal ratio than an inactive (or less active) precursor; in the simplest case, the first ligand to bind creates the catalyst of interest (m=0). The association of an additional equivalent of ligand diminishes the rate by blocking access of a substrate molecule to an open coordination site on the metal, or by diverting the system to a less active structure. A plot of ligand:metal ratio vs. catalysis rate would therefore appear as a single peak, approaching a value of zero in rate as the concentration of ligand is increased. In contrast, the benzimidazole and related CuAAC systems show persistent and considerable catalytic activity even at high ligand:Cu. This is likely due to one or both of two factors: (a) $K_2 \ll K_1$, and (b) at least two active ligand-containing catalysts or mechanistic pathways exist, one which depends on ligand:Cu, and another that is largely independent of that ratio. For all of the catalysts shown, the reaction rate in the absence of ligand was too low to be measured on our calorimeter. The accelerating ligands must therefore either be components of the active catalytic species or must enhance the concentration of active copper centers. That a complex set of equilibria are involved is further indicated by the fact that the addition of even weakly coordinating additives such as 2,6-lutidine or 2-amino-2-(hydroxymethyl)propane-1,3-diol (Tris) to the solvent system for catalyst $Cu.[(BimH)_3]_n$ removes the relatively sharp peak in the plot of rate vs. ligand:Cu, making the relationship look more like that of $Cu.(BimC_4A)_3$.

Figure 6:
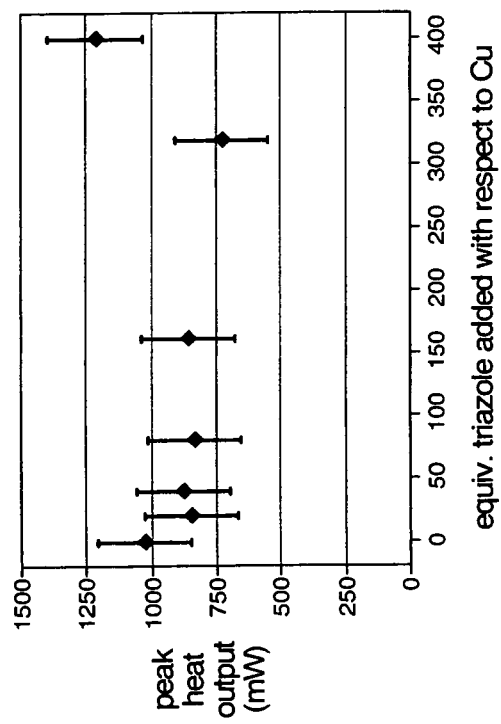
FIG. 6 illustrates a graph showing the dependence of peak reaction power (peak rate) on the amount of added 1-n-octyl-4-phenyl-1,2,3-triazole for the reaction of n-octylazide (350 mM)+phenylacetylene (450 mM), in the presence of $CuSO_4$ (2 mM), $(BimH)_3$ (4 mM), and sodium ascorbate (25 mM), 4:1 DMSO:water, at 65±2° C.

The persistence of high reaction rates in the presence of excess ligand suggests that these catalysts should also remain active in the presence of high concentrations of product triazoles, which can be expected to have some affinity for Cu(I). This has been demonstrated by the successful use of low catalysts loadings (discussed below) and by calorimetric measurements summarized in FIG. 6. Peak catalytic activity was found to be unchanged in the presence of triazole in an amount up 400 times the concentration of catalyst.

Effects of Aggregation of Long-Chain Aliphatic Azides.

Figure 7:
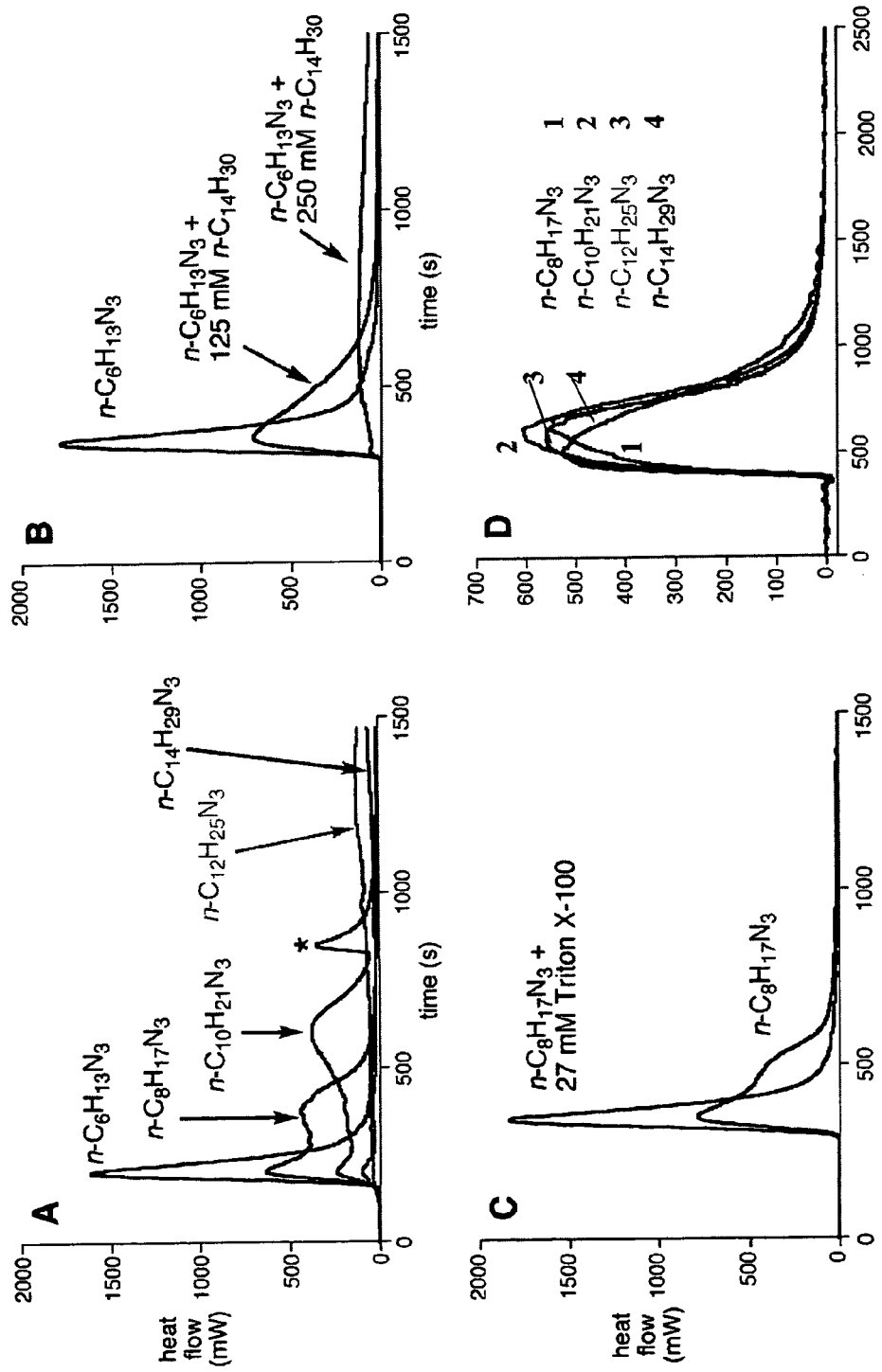
FIG. 7 illustrates a series of graphs showing corrected calorimetry data for reactions of the indicated azides and additives.

Under the typical reaction conditions in 20% (w/w) aqueous DMSO, the thermograms of reactions involving long-chain aliphatic azides (accelerated by ligand $(BimH)_3$) exhibited a distinctive two-stage reaction profile as shown in FIG. 7A. The reactions of those azides became slower, and the bimodal nature of thermograms more distinct, with elongation of the aliphatic chain. The addition of n-tetradecane to the well-behaved n-hexylazide also slowed the reaction dramatically, even though the overall concentration of azide was not changed (FIG. 7B). When the reaction was performed in the presence of the non-ionic detergent Triton-X 100 (27 mM), the thermogram reverted to the normal single-peak appearance (FIG. 7C). Single-peak behavior was also observed in pure DMSO, although the thermogram peaks were not as sharp as in the standard DMSO:water solvent system (FIG. 7D). Lastly, the use of amphiphilic ligand $(BimC_4A)_3$ in place of $(BimH)_3$ largely eliminated the bimodal behavior of aliphatic azides. All of these observations support the hypothesis that long-chain aliphatic azides partition between solvated single molecules and detergent-sensitive aggregates in the aqueous DMSO medium, and in the latter case are partially sequestered from the catalyst and alkyne.

Synthetic Evaluations.

Figures 8, 9:
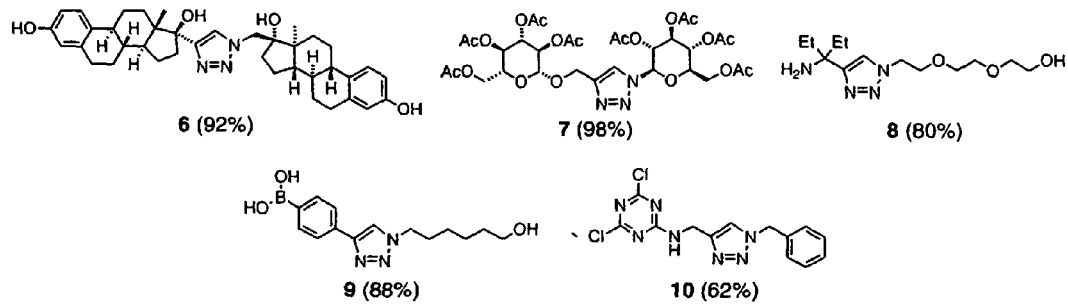
FIG. 8 illustrates a chart showing the tests of reduced catalyst loading for the reaction with phenylacetylene (0.75 M) with benzyl azide (0.75 M), 3:1 MeOH:water, 24° C.
FIG. 9 illustrates the structures of triazoles prepared by reaction of equimolar amounts of the appropriate azide and alkyne (each 10 wt %, 0.13-0.35 M, depending on molecular weight) in the presence of $CuSO_4$ (0.1 mol %), $(BimC_4A)_3$ (0.2 mol %), and sodium ascorbate (4 mol %) in 95:5 DMF:water at room temperature.
Figure 10:
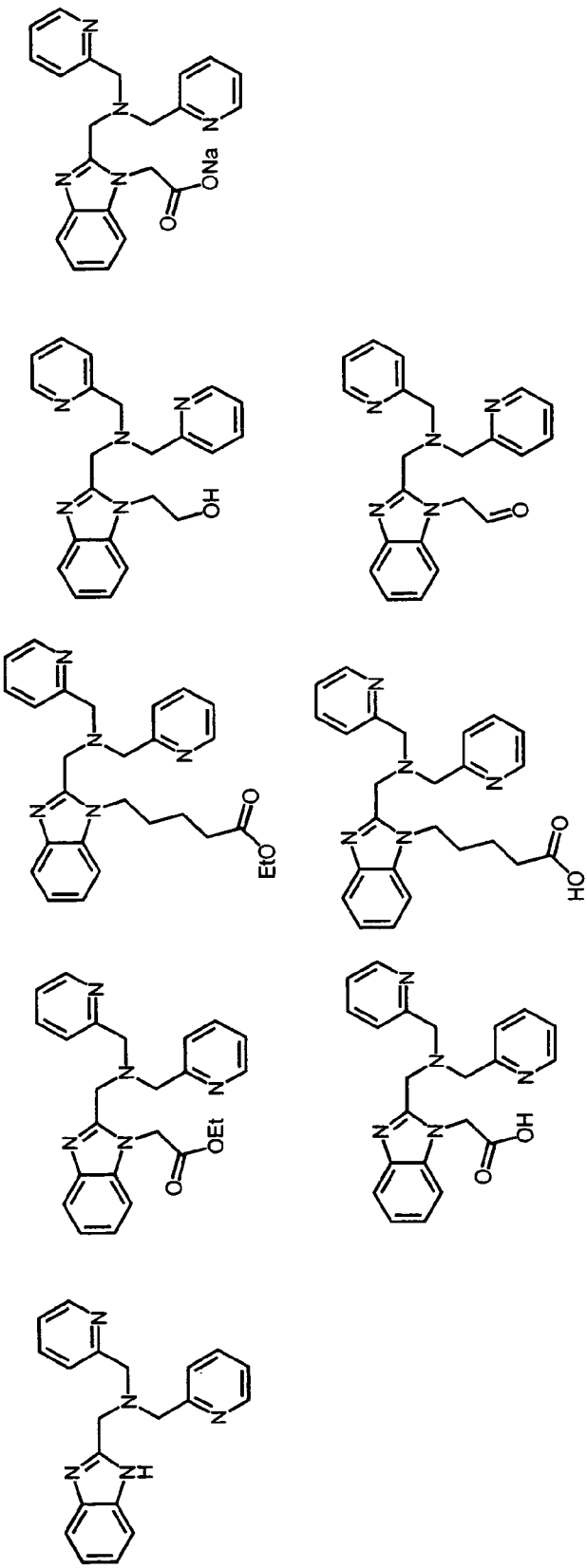
FIG. 10 illustrates additional ligands of the invention.
Figure 11:
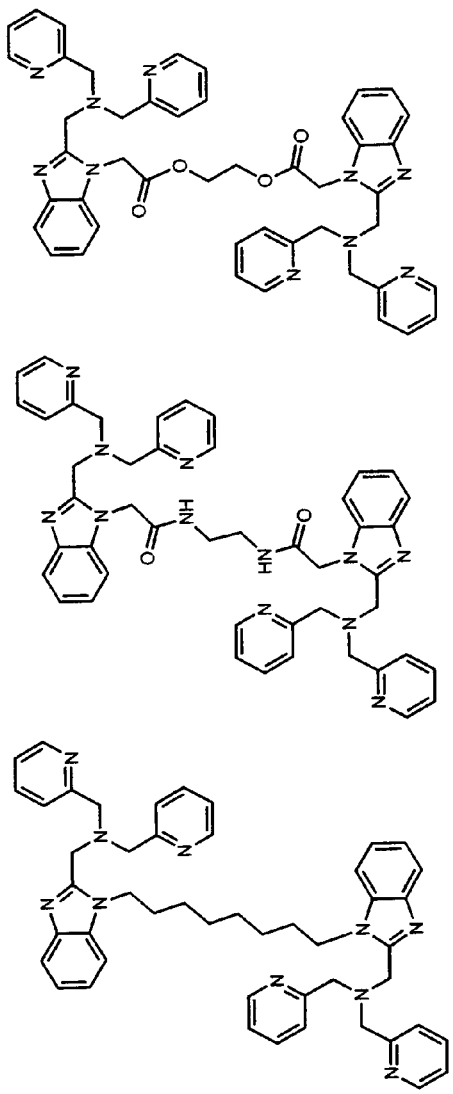
FIG. 11 illustrates additional ligands of the invention.
Figure 11:
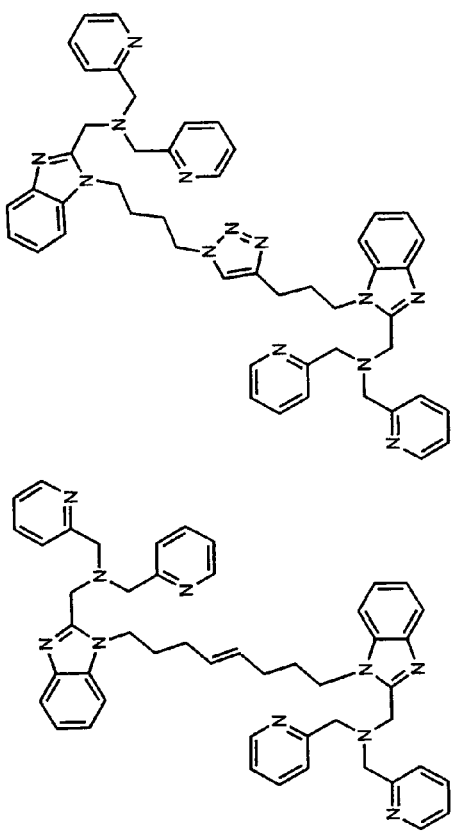

The ligands $(BimH)_3$ and $(BimC_4A)_3$, identified in the above studies as being superior under conditions of high substrate concentration, were tested along with 1 for their ability to support reactions at low catalyst loading (FIG. 8). The results mirror the findings by calorimetry, with yields following the trend $Cu.[(BimC_4A)_3] > Cu.[(BimH)_3] \gg Cu.[1]$ (entries 2, 4, 8). A maximum value of approximately $10^4$ turnovers per metal center was achieved (0.01 mol % catalyst, entry 10), allowing conveniently rapid reactions at 0.05 mol % or greater. The use of 0.0011 mol % catalyst provided a 30% yield after 3 weeks in an inert-atmosphere glove box, but no product on the bench top, suggesting that oxidation of the Cu/ascorbate system was competitive with the cycloaddition process at that point. The preformed soluble Cu(I) acetonitrile complex made a competent catalyst in the absence of ascorbate (entry 5), but cuprous iodide did not (entry 6), at least in a mixed MeOH-water solvent system. The use of diisopropylethylamine as an additive with CuI has gained some popularity, but such reactions have been found to be much slower than those performed in the presence of tris(heterocyclic methyl)amine ligands such as 1 and $(BimH)_3$ (entry 12). The successful application of $(BimC_4A)_3$ to the synthesis of other triazoles, containing steroid, carbohydrate, boronic acid, amine, alcohol, and electrophilic chlorotriazine moieties, is shown in FIG. 9. The selection of substrates is meant to illustrate the reliability and convenience of the Cu.$[(BimC_4A)_3]$ system for synthetic purposes. In addition, the water solubility of $(BimC_4A)_3$ makes the preparation of relatively hydrophobic triazoles more convenient, since a simple aqueous wash removes both the ligand and metal, leaving the product in pure form.

Tris(2-benzimidazolylmethyl)amines proved to be the most promising family of accelerating ligands for the Cu-catalyzed azide-alkyne cycloaddition reaction from among more than 100 mono-, bi-, and polydentate candidates. The benzimidazole compounds are easy to prepare and compare favorably to tris(triazolylmethyl)amines and other ligands, such as diisopropylethylamine and sulfonated bathophenanthroline that have achieved wide use. Under both preparative (high concentration, low catalyst loading) and dilute (lower substrate concentration, higher catalyst loading) conditions, tripodal benzimidazole derivatives give substantial improvements in rate and yields, with convenient workup to remove residual Cu and ligand. The relative effectiveness of ligands with different substitution patterns changes when examined under different reaction conditions.

The following examples are presented to illustrate certain aspects of the invention, but are not to be considered as limiting.

General.

Reagents and solvents were purchased from VWR/Acros or Aldrich and used without any further purification. THF, acetonitrile, diethyl ether, dichloromethane, and toluene were dried by passage through activated alumina columns. Chromatography was performed using SINGLE StEP™ prepacked MPLC columns (Thomson Instrument Company, Oceanside, Calif.). $^1$H and $^{13}$C NMR spectra were recorded on a Varian Mercury-200 spectrometer in $CDCl_3$, $CD_3OD$, $CD_3CN$ or DMSO-$d_6$ as a solvent. Routine mass spectra were obtained using an Agilent 1100 (G1946D) ESI MSD with mobile phase composed of 9:1 $CD_3CN:H_2O$ containing 0.1% $CF_3CO_2H$. GC-MS analyses were performed on an HP GCD-II (Model 5810) instrument. Elemental analyses were performed by Midwest MicroLab, LLC. Infrared spectra were recorded on MIDAC-FTIR spectrometer in KBr pellets. The following stain solutions have been used in addition to UV light with fluorescent TLC plates: phosphomolybdic acid, anisaldehyde/EtOH, and $KMnO_4/H_2O$. Reactions requiring anhydrous conditions were performed under nitrogen.

Ligand Synthesis.

Tris-benzimidazole ligand (BimH)$_3$ (Thompson, L. K.; et al. *Can. J. Chem.* 1977, 55, 878-888) and analogs H(BimH)$_2$, and (BimH)$_2$C$_2$(BimH)$_2$ (Birker, P. J. M. W. L.; et al. *Inorganic Chemistry* 1981, 20, 2408-2414) were obtained by condensation of 1,2-phenylenediamine with the corresponding tri-, di-, and tetracarboxylic acid in boiling ethylene glycol. A similar condensation reaction between 1,2-aminothiophenol and nitrilotriacetonitrile or iminodiacetonitrile was used to synthesize benzothiazole ligands (Bth)$_3$ and (H)(Bth)$_2$. The crude products usually crystallized when water was added to the cooled reaction mixture (it is important not to add water to the ethylene glycol solution while it is still hot). For the purposes of this study, the ligands were subsequently recrystallized from absolute ethanol and were found to be pure by elemental analysis. The procedure scales up without difficulty. The preparation of 1 from tripropargylamine and benzyl azide under the influence of Cu(I) sometimes suffers from incomplete reaction, the presence of colored impurities, and/or the presence of trapped copper ions in the solid product.

The mixed ligands (Bth)(BimH)$_2$ and (Bth)$_2$(BimH) were obtained by reductive amination of aldehydes 4 (Zakrzewski, A.; Janota, H. *Pestycydy* (*Warsaw*) 2004, 31-38) and 5 (Vetelino, M. G.; Coe, J. W. *Tetrahedron Lett.* 1994, 35, 219-222) (FIG. 1B) with amines (Bth)$_2$ and (H)(BimH)$_2$, respectively. N-Alkylated derivatives (BimR)$_3$ were obtained by deprotonation of (BimH)$_3$ with t-BuOK and reaction with the corresponding alkylating agent. Poor results were obtained when NaH (either dry or oil suspension) was used as the base. To produce the free carboxylate ligand (BimC$_4$A)$_3$ and its analogs, the corresponding ester was reacted with 3 equivalents of KOH in boiling aqueous ethanol. Tris(sulfonic acid) (BimH/S)$_3$ was obtained by a published procedure (Ichikawa, K.; et al. *Chem. Lett.* 2000, 796-797). Most ligands with free benzimidazole NH groups were purified by flash chromatography on a short Florisil column, eluting with 0.5% MeOH in $CH_2Cl_2$. Ordinary silica gel is not well suited to this separation due to the strong tendency of these compounds to "streak," resulting in poor recovery of the desired products.

Typical Procedure for Preparative Scale CuAAC Reactions.

The reaction flask was charged with solid sodium ascorbate, followed by the ligand, methanol (or another appropriate solvent), azide, and alkyne in that order. A solution of $CuSO_4$ in water was added, the flask was capped, and the mixture was stirred vigorously or sonicated for 5-10 minutes until all of the ascorbate was dissolved. The resulting homogeneous solution was left standing at room temperature, and periodically monitored by TLC. When reagent conversion was complete, several volumes of deionized water were added to the reaction and the precipitated triazole product was recovered by filtration. For the most part, these products were found to be >98% pure by NMR; when necessary, purification to reach this level was performed by flash chromatography, and yields are reported for the final purified products.

Details of Synthesis of Selected Ligands

Examples 1-6

Ex. (1) Tris-(2-benzimidazolylmethyl)amine (BimH)$_3$ (Thompson, L. K.; et al. *Can. J. Chem.* 1977, 55, 878-888) was prepared as follows (see FIG. 1A):

A 2-liter round-bottomed flask containing a large magnetic stir bar was charged with nitrilotriacetic acid (80 g, 418 mmol), 1,2-phenylenediamine (137.9 g, 1277 mmol), and ethylene glycol (900 mL). The flask was fitted with a reflux condenser and connected to a standard vacuum manifold. Stirring was started, and the flask was evacuated and purged with N$_2$ three times. After that, the flask was heated to reflux, and the mixture was allowed to boil for 20 hours under positive pressure of nitrogen.

The flask was allowed to cool slowly to room temperature. At that point the contents of the flask were transferred to a large beaker. 900 mL of cold water was slowly added to the reaction mixture while stirring. The crude product precipitated in the form of small violet crystals. The solid was filtered, air-dried overnight, and recrystallized twice from hot absolute ethanol to yield pure ligand as colorless needles.

Ex. (2) Tris((5,6-dimethyl-1H-benzimidazol-2-yl)methyl) amine (BimH/Me$_2$)$_3$ was prepared analogously to (BimH)$_3$ from 4,5-dimethyl-1,2-phenylenediamine and nitrilotriacetic acid.

Ex. (3) Tris-(2-benzothiazolylmethyl)amine (Bth)$_3$ was prepared analogously to (BimH)$_3$ from nitrilotriacetonitrile and 1,2-aminothiophenol.

Ex. (4) Bis-(2-benzimidazolylmethyl)amine (H)(BimH)$_2$ was prepared analogously to (BimH)$_3$ from nitrilodiacetic acid and 1,2-phenylenediamine.

Ex. (5) Bis-(2-benzothiazolylmethyl)amine (H)(Bth)$_2$ was prepared analogously to (BimH)$_3$ from nitrilodiacetonitrile and 1,2-aminothiophenol.

Ex. (6) $N^1,N^1,N^2,N^2$-tetrakis((1H-benzo[d]imidazol-2-yl) methyl)ethane-1,2-diamine (BimH)$_2$C$_2$(BimH)$_2$ was prepared analogously to (BimH)$_3$ from 1,2-phenylenediamine and ethylenediaminetetraacetic acid.

Example 7-8

Ex. (7) N,N-bis((1H-benzimidazol-2-yl)methyl)-1-(benzothiazol-2-yl)methanamine (Bth)(BimH)$_2$ Amine (H) was prepared as follows (see FIG. 1B):

(BimH)$_2$ (0.693 g, 2.5 mmol) and aldehyde 5 (0.429 g, 2.63 mmol) were dissolved in dry methanol (10 mL). The solution was cooled to 0° C. and SOCl$_2$ (30 µL) was added, followed by NaBH$_3$CN (0.630 g, 10 mmol). The reaction mixture was stirred under N$_2$ for 10 hours, after which it was transferred to a separatory funnel containing 50 mL water and 50 mL $CH_2Cl_2$. The aqueous layer was extracted twice more with $CH_2Cl_2$ (50 mL) and the combined organic fractions were extracted once with water (50 mL), and then dried over MgSO$_4$. The solvent was removed by rotary evaporation and the crude product was purified by chromatography (2% MeOH in CH$_2$Cl$_2$) on a short Florisil column.

Ex. (8) N-((1H-benzimidazol-2-yl)methyl)-1-(benzothiazol-2-yl)-N-(benzothiazol-2-ylmethyl)methanamine (Bth)$_2$(BimH) was prepared analogously to (Bth)(BimH)$_2$ from amine (H)(Bth)$_2$ and aldehyde 4 (see FIG. 1B).

Examples 9-17

Ex. (9) Triethyl 2,2',2''-(2,2',2''-nitrilotris(methylene)tris(1H-benzimidazole-2,1-diyl)) triethanoate (BimC$_1$E)$_3$ was prepared as follows:

A 50 mL dry round-bottomed flask with a magnetic stir bar was charged with tris-(2-benzimidazolylmethyl)amine (BimH)$_3$ (2.150 g, 5.28 mmol) and solid potassium tert-butoxide (1.955 g, 17.4 mmol). The flask was evacuated, purged with N$_2$, and 50 mL dry DMF was introduced via cannula with stirring. The reaction mixture was heated up in an oil bath to 50° C. Ethyl bromoacetate (2.733 g, 16.37 mmol) was added to the flask via syringe, and the reaction was stirred at 50° C. under N$_2$ atmosphere for 10 hours. The mixture was then transferred to a separatory funnel containing 100 mL water and 100 mL CH$_2$Cl$_2$. The aqueous layer was extracted twice more with CH$_2$Cl$_2$ (100 mL) and the combined organic fractions were extracted once with water (100 mL), and then dried over MgSO$_4$. The solvent was removed by rotary evaporation and the crude product was purified by crystallization from 96% EtOH.

Ex. (10) Tert-butyl 2,2',2''-(2,2',2''-nitrilotris(methylene)tris(1H-(BimC$_1$E')$_3$ was prepared analogously to (BimC$_1$E)$_3$ from tris-(2-benzimidazolylmethyl)amine (BimH)$_3$ and tert-butyl bromoacetate.

Ex. (11) Triethyl 5,5',5''-(2,2',2''-nitrilotris(methylene)tris(1H-benzimidazole-2,1-diyl))tripentanoate (BimC$_4$E)$_3$ was prepared analogously to (BimC$_1$E)$_3$ from tris-(2-benzimidazolylmethyl)amine (BimH)$_3$ and ethyl-5-bromovalerate.

Ex. (12 and 13) Triethyl 6,6',6''-(2,2',2''-nitrilotris(methylene)tris(1H-benzimidazole-2,1-diyl))trihexanoate (BimC$_5$E)$_3$ and diethyl 6,6'-(2,2'-(1H-benzo[d]imidazol-2-yl)methylazanediyl)bis(methylene)-bis(1H-benzimidazole-2,1-diyl))dihexanoate (BimH)(BimC$_5$E)$_2$ were prepared analogously to (BimC$_1$E)$_3$ from tris-(2-benzimidazolylmethyl)amine (BimH)$_3$ and ethyl-6-bromohexanoate. The reaction yielded both (BimC$_5$E)$_3$ and (BimH)(BimC$_5$E)$_2$. The products were separated and purified by chromatography on silica gel in 9:1 EtOAc:hexane.

Ex. (14) Triethyl 4,4',4''-(2,2',2''-nitrilotris(methylene)tris(1H-benzimidazole-2,1-diyl))tributanoate (BimC$_3$E)$_3$ was prepared analogously to (BimC$_1$E)$_3$ from tris-(2-benzimidazolylmethyl)amine (BimH)$_3$ and ethyl-4-bromobutanoate. Purified by crystallization from 96% ethanol.

Ex. (15) Diethyl 5,5'-(2,2'-(benzo[d]thiazol-2-ylmethylazanediyl) bis(methylene) bis(1H-benzo[d]imidazole-2,1-diyl))dipentanoate (Bth)(BimC$_4$E)$_2$ was prepared analogously to (BimC$_1$E)$_3$ from (Bth)(BimH)$_2$ and ethyl-5-bromovalerate. Purified by chromatography on silica gel in 95:5 dichloromethane:methanol.

Ex. (16) Diethyl 5,5'-(2,2'-(pyridine-2,6-diyl)bis(1H-benzo[d]imidazole-2,1-diyl))dipentanoate Py(BimC$_4$E)$_2$ was prepared analogously to (BimC$_4$E)$_3$. Purified by chromatography on silica gel in 95:5 dichloromethane:methanol.

Ex. (17) Ethyl 5-(2-((bis((1H-benzimidazol-2-yl)methyl)amino)methyl)-1H-benzo[d]imidazol-1-yl)pentanoate (BimH)$_2$(BimC$_4$E) was prepared analogously to (Bth)(BimH)$_2$ from amine (H)(BimH)$_2$ and ethyl 5-(2-formyl-1H-benzimidazol-1-yl)pentanoate. The latter was obtained by alkylation of aldehyde 4 (FIG. 1B) with ethyl-5-bromovalerate and t-BuOK at ambient temperature in DMF, and used without any purification other than a standard aqueous workup procedure.

Example 18

Ex. (18) Potassium 5,5',5''-(2,2',2''-nitrilotris(methylene) tris(1H-benzimidazole-2,1-diyl))tripentanoate (BimC$_4$A)$_3$ was prepared as follows:

A 50 mL flask fitted with a reflux condenser was charged with (BimC$_4$E)$_3$ (2.692 g, 3.4 mmol), KOH (0.168 g, 3.4 mmol), water (15 mL), and ethanol (15 mL). The reaction mixture was heated under reflux for 6 days and conversion was monitored by LCMS. When the starting material or partially hydrolyzed intermediates could no longer be detected, ethanol and water were removed by distillation at a reduced pressure to yield (BimC$_4$A)$_3$. The product was found to be of sufficient purity, and was used for all subsequent experiments as obtained.

All the other ligands with free carboxylate groups have been obtained using the same protocol. Elemental analysis revealed the presence of water in several samples; the tris (benzimidazolylmethyl)amine structure is known to be quite hygroscopic (Thompson, L. K.; et al. Can. J. Chem. 1977, 55, 878-888; Zhou, W.-H.; et al. Jiegou Huaxue 1999, 18, 204-208). Characterizing data on the various ligands are provided in Table 1.

TABLE 1

Characterization data. ("Other" includes (ESI-TOF HRMS, elemental analysis, ESI-MS, and melting points)

| Ligand | $^1$H NMR (DMSO-d$_6$) | $^{13}$C NMR (DMSO-d$_6$) | Other |
| --- | --- | --- | --- |
| (BimC$_4$A)$_3$ | 7.65-7.58 (m, 3H), 7.49-7.45 (m, 3H), 7.23-7.15 (m, 6H), 4.16 (s, 6H), 3.63 (m, 6H), 1.58-1.51 (m, 6H), 1.16-1.12 (m, 6H), 0.90-0.77 (m, 6H) | 176.20, 151.31, 142.65, 135.85, 122.89, 122.09, 119.52, 111.26, 60.97, 49.78, 43.54, 33.63, 30.02, 23.59 | calcd for C$_{39}$H$_{46}$N$_7$O$_6^+$ (M + H$^+$), 708.3504; found, 708.3501 |
| (BimC$_5$A)$_3$ | 7.65-7.61 (m, 3H), 7.44-7.24 (m, 3H), 7.20-7.13 (m, 6H), 4.14 (s, 6H), 3.34 (m, 6H), 1.70-1.52 (m, 6H), 1.40-1.00 (m, 18H) | 177.41, 151.13, 142.65, 135.72, 123.150, 122.25, 119.58, 111.19, 61.48, 49.80, 43.62, 29.97, 26.43 | calcd C$_{42}$H$_{52}$N$_7$O$_6^+$ (M + H$^+$), 750.3974; found, 750.3980 |
| (BimC$_1$A)$_3$ | 7.58-7.53 (m, 3H), 7.30-7.25 (m, 3H), 7.10-7.06 (m, 6H), 4.46 (s, 6H), 4.11 (s, 6H) | 169.78, 152.95, 142.80, 136.75, 121.81, 121.20, 119.10, 110.80, 50.78, 48.35 | calcd for C$_{30}$H$_{28}$N$_7$O$_6^+$ (M + H$^+$), 582.2096; found, 582.2090 |

TABLE 1-continued

Characterization data. ("Other" includes (ESI-TOF HRMS, elemental analysis, ESI-MS, and melting points)

| Ligand | $^1$H NMR (DMSO-$d_6$) | $^{13}$C NMR (DMSO-$d_6$) | Other |
|---|---|---|---|
| (BimC$_1$H)$_3$ | 6.80-6.75 (m, 3H), 6.63-6.59 (m, 3H), 6.38-6.31 (m, 6H), 3.31 (s, 6H), 1.65 (s, 9H) | 152.0, 136.52, 122.83, 122.15, 119.52, 110.69, 102.31, 49.84, 29.69 | calcd for C$_{27}$H$_{28}$N$_7^+$ (M + H$^+$), 450.2401; found, 450.2393. mp >250° C. (dec.) |
| (BimC$_3$A)$_3$ | 7.64-7.52 (m, 6H), 7.20-7.08 (m, 6H), 4.14 (s, 6H), 3.81-3.75 (m, 6H), 1.40-1.35 (m, 6H) | 176.07, 151.22, 142.61, 136.06, 122.77, 121.95, 119.33, 111.72, 49.81, 43.90, 34.89, 27.07 | calcd for C$_{36}$H$_{40}$N$_7$O$_6^+$ (M + H$^+$), 666.3035; found, 666.3008 |
| (Bth)$_2$(BimH) | 12.34 (s, 1H), 8.12 (dd, J = 1.0 and 6.6 Hz, 2H), 7.95 (dd, J = 1.0 and 6.6 Hz, 2H), 7.54-7.42 (m 6H), 7.20-7.15 (m, 2H), 4.49 (s, 4H), 4.21 (s, 2H) | 171.54, 152.49, 150.03, 142.76, 134.41, 133.56, 125.55, 124.54, 122.0, 121.84, 121.64, 120.77, 118.22, 110.91 | calcd for C$_{24}$H$_{19}$N$_5$S$_2$: C, 65.28; H, 4.34; N, 15.86; S, 14.52. found: C, 65.17; H, 4.40; N, 15.78; S, 14.67. mp 190° C. |
| (Bth)(BimH)$_2$ | 8.06 (dd, J = 1.2 and 7.8 Hz, 1H), 7.94 (dd, J = 1.2 and 7.8 Hz, 1H), 7.60-7.40 (m, 6H), 7.19-7.15 (m, 4H), 4.39 (s, 2H), 4.22 (s, 4H) | 172.56, 153.66, 152.20, 135.59, 126.63, 125.60, 123.10, 122.90, 122.30, 55.78, 51.99 | calcd for C$_{24}$H$_{21}$N$_6$S$^+$ (M + H$^+$), 425.1543; found, 425.1561. calcd for (Bth)(BimH)$_2$·4H$_2$O C, 58.05; H, 5.68; N, 16.92; S, 6.46. found: C, 58.59; H, 5.41; N, 17.03; S, 7.01 mp 105° C. |
| (BimH)$_2$(BimC$_4$A) | 7.75-7.72 (m, 1H), 7.57-7.42 (m, 4H), 7.15-7.09 (m, 7H), 3.86 (s, 4H), 3.78 (s, 2H), 2.29-2.26 (m, 2H), 1.95-1.85 (m, 2H), 1.72-1.67 (m, 2H) | 177.34, 152.60, 150.52, 135.79, 122.88, 122.10, 119.58, 112.98, 111.14, 54.19, 44.60, 29.75, 23.96 | calcd for C$_{29}$H$_{30}$N$_7$O$_2^+$ (M + H$^+$), 508.2458; found, 508.2461 |
| Py(BimC$_4$A)$_2$ | 8.34-8.15 (m, 3H), 7.76-7.68 (m, 4H), 7.35-7.23 (m, 4H), 4.79 (m, 4H), 1.82-1.64 (m, 8H), 1.26-1.22 (m, 4H) | 176.49, 150.43, 150.27, 142.91, 139.35, 136.95, 126.16, 123.94, 123.04, 120.28, 112.13, 45.12, 41.23, 30.91, 24.22 | calcd for C$_{29}$H$_{30}$N$_5$O$_4^+$ (M + H$^+$), 512.2292; found, 512.2302 |
| (BimH/Me$_2$)$_3$ | 12.14 (s, 3H), 7.29 (s, 6H), 3.99 (s, 6H), 2.27 (s, 18H) | 151.74, 130.64, 119.42, 111.97, 63.46, 52.0 | calcd for C$_{30}$H$_{34}$N$_7^+$ (M + H$^+$), 492.2870; found, 492.2861. mp >250° C. (dec) |
| (Bth)-(BimC$_4$A)$_2$ | 8.05-8.01 (m, 1H), 7.92-7.88 (m, 1H), 7.62-7.35 (m, 6H), 7.35-7.14 (m, 4H), 4.43 (s, 2H), 4.27 (s, 4H), 4.16 (m, 4H), 1.73-1.66 (m, 4H), 1.53-1.50 (m, 4H), 1.26-1.22 (m, 4H) | 175.86, 171.96, 153.50, 151.31, 142.77, 135.95, 135.52, 126.63, 125.62, 123.07, 122.98, 122.79, 122.02, 119.58, 111.2, 97.26, 55.50, 50.58, 43.91, 30.41, 24.34 | calcd for C$_{34}$H$_{37}$N$_6$O$_4$S$^+$ (M + H$^+$), 625.2592; found, 625.2580 |
| (BimH)-(BimC$_5$A)$_2$ | 7.61-7.42 (m, 6H), 7.22-7.12 (m, 6H), 4.15 (s, 6H), 3.24 (m, 4H), 1.74-1.67 (m, 4H), 1.40-0.9 (m, 12H) | 177.69, 154.41, 154.13, 151.91, 142.75, 141.95, 140.97, 135.93, 122.80, 122.00, 121.15, 120.54, 119.61, 115.86, 110.93, 53.83, 52.76, 50.35, 43.59, 30.00, 26.90, 26.64 | calcd for C$_{36}$H$_{42}$N$_7$O$_4^+$ (M + H$^+$), 636.3293; found, 636.3289 |
| (BimH)$_3$ | 12.45 (s, 3H), 7.57 (m, 6H), 7.17 (m, 6H), 4.15 (s, 6H) | 152.18, 143.27, 134.20, 122.02, 121.23, 118.58, 111.31, 51.46 | calcd for (BimH)$_3$·H$_2$O: C$_{24}$H$_{23}$N$_7$O$^+$: C, 67.75; H, 5.45; N, 23.04. found: C, 67.26; H, 5.45; N, 22.81 mp >250° C. (dec) |
| (Bth)$_3$ | 8.16-8.12 (m, 3H), 7.98-7.94 (m, 3H), 7.50-7.43 (m, 6H), 4.40 (s, 6H) | 170.87, 152.82, 134.86, 126.16, 125.19, 122.56, 122.39, 55.84 | calcd for C$_{24}$H$_{18}$N$_4$S$_3$: C, 62.85; H, 3.96; N, 12.22; S, 20.97. found: C, 62.53; H, 4.03; N, 12.13; S, 21.07. mp 141° C. |
| (H)(BimH)$_2$ | 12.27 (s, 2H), 7.48 (s, 4H), 7.16-7.07 (m, 4H), 3.98 (s, 4H) | 154.63, 122.18, 119.05, 111.77, 47.17 | calcd for (H)(BimH)$_2$·H$_2$O, C$_{16}$H$_{17}$N$_5$O: C, 65.07; H, 5.80; N, 23.71. found: C, 66.30; H, 5.63; N, 23.98. mp 248° C. (dec) |

TABLE 1-continued

Characterization data. ("Other" includes (ESI-TOF HRMS, elemental analysis, ESI-MS, and melting points)

| Ligand | $^1$H NMR (DMSO-$d_6$) | $^{13}$C NMR (DMSO-$d_6$) | Other |
|---|---|---|---|
| (H)(Bth)$_2$ | 8.09 (dd, J = 1.8 and 7.2 Hz, 2H), 7.92 (dd, J = 1.8 and 7.2 Hz, 2H), 7.53-7.37 (m, 4H), 4.28 (s, 4H) | 174.92, 153.76, 135.30, 126.61, 125.43, 122.93, 97.25, 51.10 | calcd for $C_{16}H_{13}N_3S_2$: C, 61.71; H, 4.21; N, 13.49; S, 20.59. found: C, 61.57; H, 4.24; N, 13.29; S, 20.88 mp 117° C. |
| (BimC$_4$E)$_3$ | 7.66-7.61 (m, 3H), 7.46-7.42 (m, 3H), 7.21-7.16 (m, 6H), 4.15 (s, 6H), 3.97 (q, J = 7.2 Hz, 6H), 3.61 (t, J = 7.4 Hz, 6H), 1.86 (t, J = 7.4 Hz, 6H), 1.14 (m, 6H), 1.12 (t, J = 7.2 Hz, 9H), 0.79 (m, 6H) | 172.83, 151.37, 142.65, 135.68, 123.10, 122.29, 119.62, 110.90, 60.31, 49.76, 42.87, 33.57, 29.22, 21.76, 14.75 | (M + H$^+$) 792.4 (M + Na$^+$) 814.4 |
| (BimC$_1$E')$_3$ | 7.62-7.57 (m, 3H), 7.47-7.42 (m, 3H), 7.20-7.16 (m, 6H), 5.14 (s, 6H), 3.98 (s, 6H), 1.10 (s, 27H) | 167.74, 152.00, 142.58, 136.34, 123.22, 122.43, 119.68, 110.72, 82.56, 50.51, 45.71, 27.96 | calcd for $C_{42}H_{51}N_7O_6$: C, 67.27; H, 6.85; N, 13.07; O, 12.80. found: C, 67.17; H, 6.83; N, 13.14; O, 12.66. (Note: analysis for oxygen was performed.) mp 205° C. |
| (BimC$_1$E)$_3$ | 7.51-7.61 (m, 3H), 7.53-7.48 (m, 3H), 7.24-7.19 (m, 6H), 5.28 (s, 6H), 4.0 (s, 6H), 3.80 (q, J = 7 Hz, 6H), 0.99 (t, J = 7 Hz, 9H) | 168.67, 151.90, 142.52, 136.31, 123.22, 122.52, 119.57, 110.82, 61.85, 51.05, 44.97, 14.37 | (M + H$^+$) 666.3 (M + Na$^+$) 688.3 mp 168° C. |
| (BimH)$_2$C$_2$-(BimH)$_2$ | 7.57-7.55 (m, 4H), 7.43-7.40 (m, 4H), 7.19-7.10 (m, 8H), 4.02 (s, 8H), 2.88 (s, 4H) | 153.17, 143.75, 134.83, 122.60, 121.84, 119.04, 111.88, 52.11, 51.57 | (M + H$^+$) 581.3 (M + Na$^+$) 603.3 mp 160° C. (dec) |

Example 19

Determination of Second-Order Rate Constants

Experimental Method.

Reagent stock solutions were freshly prepared before use. In a typical experiment, reactions were set up in the first column of a deep-well polypropylene microtiter plate (2.5 mL well volume). 100 μL of 30% $H_2O_2$ and 100 μL of ethanol were dispensed into all other wells.

The reactions were started by the addition of the final component (typically CuSO$_4$ solution). Aliquots of 100 μL were taken at 1-5 minute intervals from the reaction wells with a multichannel pipetman, and transferred to the subsequent columns of wells for quenching. After the desired number of aliquots have been quenched in this fashion, the contents of the plate were transferred to a standard polystyrene 96-well plate for analysis.

LC-MS analysis was performed on an Agilent 1100 (G1946D) instrument, equipped with a 35 mm Agilent ZORBAX® 3.5μ or 1.8μ SB-C18 column. The elution solvent for the detection of 1-benzyl-4-phenyl-1,2,3-triazole was 55:45 $H_2O:CH_3CN$, with 0.5% TFA. Analysis of the other triazole products required a solvent gradient (typically from 50:50 to 25:75 $H_2O:CH_3CN$, 0.5% TFA over the course of 4-5 minutes). Detection was performed in single ion mode (SIM), which typically allowed for quantitative triazole detection down to 0.1 μM. 1-benzyl-4-phenyl-1,2,3-triazole-d7 was used as internal reference for all experiments.

Data Treatment (Adapted from the World-Wide-Web Website of chem(dot)arizona(dot)edu/~salzmanr/480a/480ants/int2ord/int2ord.html)

The standard integrated rate law for a bimolecular reaction $$A(\text{azide}) + B(\text{alkyne}) \rightarrow P(\text{triazole})$$

was constructed for the present situation in which $[B]_0 = n[A]_0$, (n>1), as follows;

$$[A] = [A]_0 - [P], [B] = [B]_0 - [P]$$

$$\frac{d[P]}{dt} = k([A]_0 - [P])([B]_0 - [P]) = k([A]_0 - [P])(n[A]_0 - [P])$$

$$\frac{dP}{([P] - [A]_0)([P] - n[A]_0)} = kdt.$$

Rewriting by the method of partial fractions, $$\frac{1}{([P] - [A]_0)([P] - n[A]_0)} = \qquad (1)$$

$$\frac{X}{[P] - [A]_0} + \frac{Y}{[P] - n[A]_0} = \frac{X([P] - n[A]_0) + Y([P] - [A]_0)}{([P] - [A]_0)([P] - n[A]_0)}$$

so, $$1 = X([P] - n[A]_0) + Y([P] - [A]_0)$$

$$1 = X[P] + Y([P]) - [A]_0(nX + Y)$$

giving $$Y = -X \text{ and } 1 = -nX[A]_0 - [A]_0 Y$$

$$X = \frac{1}{([A]_0 - n[A]_0)}$$

substitute into (1)

$$\frac{1}{([P]-[A]_0)([P]-n[A]_0)} = \frac{1}{(n-1)[A]_0([P]-n[A]_0)} - \frac{1}{(n-1)[A]_0([P]-[A]_0)}$$

therefore $$\int \frac{d[P]}{(n-1)[A]_0([P]-n[A]_0)} - \int \frac{d[P]}{(n-1)[A]_0([P]-[A]_0)} = k\int dt$$

integrate (from 0 to [P], and 0 to t) to get $$\ln\left(\frac{[P]-n[A]_0}{n([P]-[A]_0)}\right) = (n-1)[A]_0 kt \quad (2)$$

Or, solving for [P]:

$$[P] = \frac{n[A]_0(1-e^{(n-1)[A]_0 kt})}{(1-e^{(n-1)[A]_0 kt})}. \quad (3)$$

Equations (2) and (3) were used to find the value of k ($k_{obs}$) that gives the best fit curve to the experimental data of [P] vs. time.

FIG. 2 summarizes the rate data. Note that the rate constants obtained here are really specific activities at 0.10 mM Cu catalyst concentration. Very similar results were obtained at pH 8 in the presence of 180 mM vs. 10 mM HEPES buffer. Kinetics Data for FIG. 2.

FIG. 2B. Conditions: 1 mM $BnN_3$, 2 mM PhCCH, 0.1 mM $CuSO_4$, 0.2 mM ligand, 4:1 DMSO:HEPES (180 mM), 25 mM NaAsc; pH verified with meter after ascorbate addition. The dots mark observed data points; the solid line is the best second-order fit; an initial "burst" of catalytic activity was not counted in the reported rate constants. Experimental error in rate constants upon repeat measurement is <15% (usually ca. 10%), except where noted.

FIG. 2C. Conditions: 1 mM $BnN_3$, 2 mM PhCCH, 0.1 mM $CuSO_4$, 0.2 mM ligand, 4:1 DMSO:HEPES (180 mM), 25 mM NaAsc; pH verified with meter after ascorbate addition. The dots mark observed data points; the solid line is the best second-order fit; an initial "burst" of catalytic activity was not counted in the reported rate constants. Experimental error in rate constants upon repeat measurement is <15% (usually ca. 10%), except where noted.

FIG. 2D. Conditions: 1 mM $BnN_3$, 2 mM PhCCH, 0.1 mM $CuSO_4$, 0.2 mM ligand, 4:1 DMSO:water, 25 mM NaAsc; pH verified with meter after ascorbate addition. The dots mark observed data points; the solid line is the best second-order fit; an initial "burst" of catalytic activity was not counted in the reported rate constants. Experimental error in rate constants upon repeat measurement is <15% (usually ca. 10%), except where noted. Plots for the HEPES part of this FIG. are the same as used for FIG. 2B.

Ligand:Cu Ratio for TBTA (Ligand 1):

[azide]=[alkyne]=1.0 mM; [$CuSO_4$]=0.1 mM; [ligand]= varies; 4:1 DMSO:$H_2O$ containing 40 mM Na ascorbate, 24° C. Product concentration values were obtained with reference to a non-calibrated internal standard. Therefore, these values are accurate in a relative, but not an absolute, sense.

Example 20

Ligand Screening by Calorimetry

Calorimetry was performed in an Omnical INSIGHT® 10-channel reaction calorimeter using 40 mL glass vials. In a typical run all the reaction components but one were introduced into the vials inside an inert atmosphere glovebox, and vials were sealed with septum caps. The last reaction component to be added was placed in a Hamilton gastight syringe. The vials and syringes were then allowed to equilibrate inside the preheated instrument (65° C.) for 30 minutes. The reaction was started in all vials by depressing all of the syringes simultaneously. Two vials out of ten were charged only with solvent to obtain readings allowing for compensation for the heat of mixing. The thermograms registered in these two channels upon addition of the last component were used to construct the baseline for the other 8 channels.

Since heat is not transferred to the instrument sensor instantaneously, the thermogram registered by the instrument is dependent on the characteristics of the instrument and reaction vessel. Correction for these extraneous factors must be applied to the recorded thermograms to obtain instrument-independent data (Rosner, T.; et al. *J. Am. Chem. Soc.* 2001, 123, 1848-1855; Liu, J.-S.; et al. *Thermochimica Acta* 1994, 236, 113-122). The appropriate dynamic correction function is built into the instrument operating software. Use of vendor supplied software produces the same result as manual correction.

It is important to note that the sensitivity of the instrument is limited, such that a significant fraction of heat is lost or goes unrecorded if the reactions are not strongly exothermic, as evidenced by the production of substantial quantities of triazole for reactions that did not register substantial thermogram signals, such as those without added ligand. Such reactions that failed to produce a signal in the calorimeter were classified as identifying "inactive" ligands. By the same token, catalysts such as Cu.1 that give observable, but not very strong, calorimetry signals cannot be fully analyzed by converting thermograms to completion curves, because a significant amount of the total energy output is lost below the detection threshold of the instrument. TBTA (1) falls into this category, classified as "moderate" ligands. "Well-behaved," thermograms as defined in the text exhibit completion curves that can be fit to second-order kinetics in the manner of Blackmond and coworkers (LeBlond, C.; et al. *Thermochimica Acta* 1996, 289, 189-207; Blackmond, D. G.; et al. *Org. Proc. Res. Devel.* 1999, 3, 275-280; Mathew, J. S.; et al. *J. Org. Chem.* 2006, 71, 4711-4722). However, peak power values (i.e., maximum reaction rate) provided a reproducible relative measure of relative catalytic efficiency.

Ligands were screened under the following conditions: 250 mM benzyl azide, 454 mM phenylacetylene, 2 mM $CuSO_4$, 4 mM ligand, 25 mM sodium ascorbate. Phenylacetylene was the last component added. Initial screening was performed with at least two independent trials for each ligand. Candidates showing promising activity were then examined with at least three independent trials to obtain reliable estimations of experimental error.

Significant observations include the following:

(a) Sulfonated bathophenanthroline 2 (FIG. 1C), an excellent ligand at more dilute concentrations, performed quite badly here, ranking at the bottom of the "moderate" category. There are several possible reasons for this, which have not been investigated, and so limited importance is placed on this observation at present.

(b) Phosphines are popular ligands for Cu(I), but several monodentate and chelating diphosphines gave rise to poor catalysts for CuAAC.

(c) N-Heterocyclic carbenes: Complex S1 has recently been reported to be a moderately-active catalyst for the CuAAC reaction (Díez-González, S.; et al. Chem. Eur. J. 2006, 12, 7558-7564). However, this complex yielded no detectable exothermic heat flow in the calorimetry assay. Therefore, while it is an active catalyst in our hands, it is not competitive with the other systems described here under the calorimetry conditions. Complex S2, is the most effective system described by Nolan, et al. Complex S3, a binuclear derivative, was markedly more effective than S1, in the range of TBTA (1). S1 and S3 were kindly provided by Dr. Timo Wiede, of the laboratory of Profs. V. Fokin and K. B. Sharpless. The highly encouraging result with S3 is being pursued there.

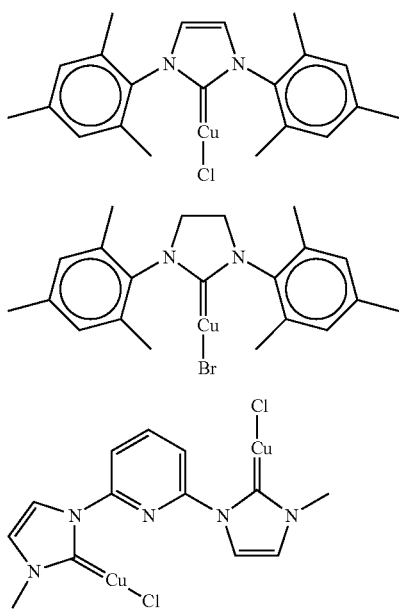

Typical Procedure for Preparative-Scale Reactions (FIG. 8).

The reaction flask was charged with solid sodium ascorbate, followed by the ligand, methanol, azide, and alkyne in that order. A solution of $CuSO_4$ in water was added, the flask was capped, and the mixture was stirred vigorously or sonicated for 10 minutes. The resulting homogeneous solution was left standing at room temperature, and periodically monitored by TLC. When reagent conversion was complete, several volumes of deionized water were added to the reaction and the precipitated triazole product was recovered by filtration. For the most part, these products were found to be >98% pure by NMR; when necessary, purification to reach this level was performed by flash chromatography, and yields are reported for the final purified products.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A multidentate ligand of Formula (II):

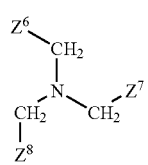

Formula (II)

wherein each of $Z^6$, $Z^7$, and $Z^8$ is a 2-benzimidazolyl group bearing a substituent, $—(CH_2)_m—R^5$;

each $R^5$ is independently selected from the group consisting of $—C(O)OH$, $—C(O)OM$, $—C(O)OR^6$, $—C(O)NHR^7$, and $—C(O)R^8$;

each M is an alkali metal ion or ammonium ion;

each $R^6$ and $R^7$ is independently a $C_1$-$C_6$-alkyl group;

each $R^8$ is independently H or a $C_1$-$C_6$-alkyl group;

and each m is independently 1, 2, 3, 4, 5, 6, 7, 8, 9, or 10.

2. Potassium 5,5',5''-(2,2',2''-nitrilotris(methylene)tris (1H-benzimidazole-2,1-diyl))tripentanoate.

* * * * *

UNITED STATES PATENT AND TRADEMARK OFFICE
CERTIFICATE OF CORRECTION

PATENT NO. : 8,563,738 B2
APPLICATION NO. : 12/733730
DATED : October 22, 2013
INVENTOR(S) : Finn et al.

It is certified that error appears in the above-identified patent and that said Letters Patent is hereby corrected as shown below:

In the Specifications

Column 5,
Line 17, "–(CH$_2$)–R$^1$" should be -- –(CH$_2$)$_n$–R$^1$ --.

Column 6,
Formula (III) appearing at lines 41-47 should be depicted as follows:

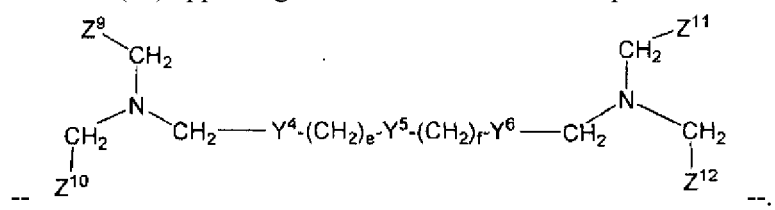

-- --.

Column 6 (continued),
Line 52, "1 and L," should be
-- 1 and 2 positions; and each of e and f is
independently 1, 2, 3, 4, or 5. Each of $Z^9$, $Z^{10}$, $Z^{11}$ --.

Column 11,
Line 5, "(BimC$_3$E)$_3$" should be -- (BimC$_1$E)$_3$ --.

Column 12,
Line 31, "*Chem. Eur.* 12006" should be -- *Chem. Eur. J.* 2006 --.

Column 14,
Line 31, "0.0011 mol%" should be -- 0.001 mol% --.

Column 17,
Line 31, after "tris(1H-" insert -- benzimidazole-2,1-diyl))triethanoate --.

Signed and Sealed this
Twenty-ninth Day of April, 2014

Michelle K. Lee
*Deputy Director of the United States Patent and Trademark Office*